(12) United States Patent
Han et al.

(10) Patent No.: US 11,246,345 B2
(45) Date of Patent: Feb. 15, 2022

(54) AEROSOL GENERATING DEVICE PROVIDED WITH ROTARY HEATER

(71) Applicant: KT&G CORPORATION, Daejeon (KR)

(72) Inventors: Jung Ho Han, Daejeon (KR); Hun Il Lim, Seoul (KR); Jong Sub Lee, Seongnam-si (KR); Dae Nam Han, Daejeon (KR); Jin Young Yoon, Seoul (KR); Young Lea Kim, Seoul (KR); Jang Uk Lee, Seoul (KR); Ji Soo Jang, Seoul (KR); Wang Seop Lim, Anyang-si (KR); Moon Bong Lee, Seoul (KR); Soung Ho Ju, Daejeon (KR)

(73) Assignee: KT&G CORPORATION, Daejeon (KR)

( * ) Notice: Subject to any disclaimer, the term of this patent is extended or adjusted under 35 U.S.C. 154(b) by 11 days.

(21) Appl. No.: 16/604,458

(22) PCT Filed: Apr. 10, 2018

(86) PCT No.: PCT/KR2018/004181
§ 371 (c)(1),
(2) Date: Oct. 10, 2019

(87) PCT Pub. No.: WO2018/190607
PCT Pub. Date: Oct. 18, 2018

(65) Prior Publication Data
US 2020/0154768 A1    May 21, 2020

(30) Foreign Application Priority Data

Apr. 11, 2017  (KR) .................... 10-2017-0046938
Jun. 19, 2017  (KR) .................... 10-2017-0077586
Sep. 29, 2017  (KR) .................... 10-2017-0128293

(51) Int. Cl.
*A24F 13/00* (2006.01)
*A24F 17/00* (2006.01)
(Continued)

(52) U.S. Cl.
CPC .............. *A24F 40/46* (2020.01); *A24F 40/20* (2020.01); *A24F 40/40* (2020.01); *A24F 40/48* (2020.01);
(Continued)

(58) Field of Classification Search
CPC ...... A24F 47/002; A24F 47/008; A24F 40/00; A24F 40/20; A24F 40/46
(Continued)

(56) References Cited

U.S. PATENT DOCUMENTS 2,638,904 A    5/1953   Mitchell
4,637,407 A    1/1987   Bonanno et al.
(Continued)

FOREIGN PATENT DOCUMENTS

CA    2 973 143 A1    8/2016
CH      310239 A     12/1955
(Continued)

OTHER PUBLICATIONS

Office Action dated Dec. 11, 2019 in Korean Application No. 10-2018-0010836.
(Continued)

*Primary Examiner* — Hae Moon Hyeon
(74) *Attorney, Agent, or Firm* — Sughrue Mion, PLLC

(57) ABSTRACT

An aerosol generating device provided with a rotary heater includes a casing having a hollow shape and including a path in which a cigarette is accommodated; a rotating member rotatably coupled to the casing; and a heater which has an end portion located inside the path to be inserted into the cigarette accommodated in the path, is connected to the
(Continued)

rotating member to rotate along with the rotating member, and heats the cigarette when electricity is applied to the heater.

11 Claims, 25 Drawing Sheets

(51) Int. Cl.

| | |
|---|---|
| *A24F 25/00* | (2006.01) |
| *A24F 40/46* | (2020.01) |
| *A24F 40/90* | (2020.01) |
| *A24F 40/40* | (2020.01) |
| *A24F 40/85* | (2020.01) |
| *A46B 15/00* | (2006.01) |
| *H05B 3/03* | (2006.01) |
| *H05B 3/06* | (2006.01) |
| *H02J 7/00* | (2006.01) |
| *A24F 40/48* | (2020.01) |
| *A24F 40/20* | (2020.01) |
| *A24F 40/57* | (2020.01) |
| *A24F 40/51* | (2020.01) |
| *A24F 40/60* | (2020.01) |
| *A24D 1/20* | (2020.01) |

(52) U.S. Cl.
CPC .............. *A24F 40/51* (2020.01); *A24F 40/57* (2020.01); *A24F 40/60* (2020.01); *A24F 40/85* (2020.01); *A24F 40/90* (2020.01); *A46B 15/0055* (2013.01); *A46B 15/0097* (2013.01); *H02J 7/0044* (2013.01); *H05B 3/03* (2013.01); *H05B 3/06* (2013.01); *A24D 1/20* (2020.01); *A46B 2200/3013* (2013.01)

(58) Field of Classification Search
USPC .................................................. 131/328, 329
See application file for complete search history.

(56) References Cited

U.S. PATENT DOCUMENTS

| | | |
|---|---|---|
| 5,144,962 A | 9/1992 | Counts et al. |
| 5,240,012 A | 8/1993 | Ehrman et al. |
| 5,249,586 A | 10/1993 | Morgan et al. |
| 5,388,594 A | 2/1995 | Counts et al. |
| 5,465,738 A | 11/1995 | Rowland |
| 5,479,948 A | 1/1996 | Counts et al. |
| 5,591,368 A | 1/1997 | Fleischhauer et al. |
| 5,666,977 A | 9/1997 | Higgins et al. |
| 5,878,752 A | 3/1999 | Adams et al. |
| 6,053,176 A * | 4/2000 | Adams .................... A24F 40/60 131/329 |
| 6,418,938 B1 | 7/2002 | Fleischhauer et al. |
| 6,532,965 B1 | 3/2003 | Abhulimen et al. |
| 6,615,840 B1 | 9/2003 | Fournier et al. |
| 6,810,883 B2 | 11/2004 | Felter et al. |
| 7,861,726 B1 | 1/2011 | Lukasavitz |
| 8,375,959 B2 | 2/2013 | Dittrich et al. |
| 8,419,085 B2 | 4/2013 | Kim et al. |
| 8,752,545 B2 | 6/2014 | Buchberger |
| 8,851,081 B2 | 10/2014 | Fernando et al. |
| 8,973,587 B2 | 3/2015 | Liu |
| 9,078,472 B2 | 7/2015 | Liu |
| 9,078,473 B2 | 7/2015 | Worm et al. |
| 9,271,528 B2 | 3/2016 | Liu |
| 9,320,299 B2 | 4/2016 | Hearn et al. |
| 9,423,152 B2 | 8/2016 | Ampolini et al. |
| 9,427,023 B2 | 8/2016 | Liu |
| 9,497,991 B2 | 11/2016 | Besso et al. |
| 9,499,332 B2 | 11/2016 | Fernando et al. |
| 9,516,899 B2 | 12/2016 | Plojoux et al. |
| 9,560,883 B2 | 2/2017 | Hawes |
| 9,603,388 B2 | 3/2017 | Fernando et al. |
| 9,655,383 B2 | 5/2017 | Holzherr et al. |
| 9,693,587 B2 | 7/2017 | Plojoux et al. |
| 9,723,871 B2 | 8/2017 | Xiang |
| 9,814,263 B2 | 11/2017 | Cochand et al. |
| 9,854,841 B2 | 1/2018 | Ampolini et al. |
| 9,854,845 B2 | 1/2018 | Plojoux et al. |
| 9,894,934 B2 | 2/2018 | Li et al. |
| 9,918,494 B2 | 3/2018 | Mironov et al. |
| 9,955,724 B2 | 5/2018 | Lord |
| 9,986,760 B2 | 6/2018 | Macko et al. |
| 9,999,247 B2 | 6/2018 | Ruscio et al. |
| 10,015,990 B2 | 7/2018 | Mironov |
| 10,031,183 B2 | 7/2018 | Novak, III et al. |
| 10,070,667 B2 | 9/2018 | Lord et al. |
| 10,104,911 B2 | 10/2018 | Thorens et al. |
| 10,130,780 B2 | 11/2018 | Talon |
| 10,136,673 B2 | 11/2018 | Mironov |
| 10,159,283 B2 | 12/2018 | Mironov |
| 10,194,697 B2 | 2/2019 | Fernando et al. |
| 10,299,513 B2 | 5/2019 | Perez et al. |
| 10,368,584 B2 | 8/2019 | Fernando et al. |
| 10,439,419 B2 | 10/2019 | Bernauer et al. |
| 10,440,987 B2 | 10/2019 | Zeng et al. |
| 10,448,670 B2 | 10/2019 | Talon et al. |
| 10,492,542 B1 | 12/2019 | Worm et al. |
| 10,548,350 B2 | 2/2020 | Greim et al. |
| 10,555,553 B2 | 2/2020 | Binassi et al. |
| 10,588,351 B2 | 3/2020 | Ricketts |
| 10,645,971 B2 | 5/2020 | Zitzke |
| 10,668,058 B2 | 6/2020 | Rose et al. |
| 10,716,329 B2 | 7/2020 | Matsumoto et al. |
| 10,813,174 B2 | 10/2020 | Schneider et al. |
| 10,881,143 B2 | 1/2021 | Suzuki et al. |
| 11,039,642 B2 | 6/2021 | Zuber et al. |
| 11,147,316 B2 | 10/2021 | Farine et al. |
| 2004/0261802 A1 | 12/2004 | Griffin et al. |
| 2005/0045198 A1 | 3/2005 | Larson et al. |
| 2005/0172976 A1 | 8/2005 | Newman et al. |
| 2008/0001052 A1 | 1/2008 | Kalous et al. |
| 2010/0307518 A1 | 12/2010 | Wang |
| 2011/0155151 A1 | 6/2011 | Newman et al. |
| 2011/0209717 A1 | 9/2011 | Han |
| 2011/0290248 A1 | 12/2011 | Schennum |
| 2011/0290269 A1 | 12/2011 | Shimizu |
| 2012/0247494 A1 | 10/2012 | Oglesby et al. |
| 2013/0037041 A1 | 2/2013 | Worm et al. |
| 2013/0213419 A1 | 8/2013 | Tucker et al. |
| 2013/0284192 A1 | 10/2013 | Peleg et al. |
| 2013/0319439 A1 | 12/2013 | Gorelick et al. |
| 2013/0340775 A1 | 12/2013 | Juster et al. |
| 2014/0020698 A1 | 1/2014 | Fiebelkorn |
| 2014/0096782 A1 | 4/2014 | Ampolini et al. |
| 2014/0116455 A1 | 5/2014 | Youn |
| 2014/0246035 A1 | 9/2014 | Minskoff et al. |
| 2014/0299137 A1 | 10/2014 | Kieckbusch et al. |
| 2014/0301721 A1 | 10/2014 | Ruscio et al. |
| 2014/0305448 A1 | 10/2014 | Zuber et al. |
| 2014/0318559 A1 | 10/2014 | Thorens et al. |
| 2014/0345633 A1 | 11/2014 | Talon et al. |
| 2014/0345634 A1 | 11/2014 | Zuber et al. |
| 2014/0363145 A1 | 12/2014 | Plojoux et al. |
| 2015/0007838 A1 | 1/2015 | Fernando et al. |
| 2015/0013696 A1 | 1/2015 | Plojoux et al. |
| 2015/0020832 A1 | 1/2015 | Greim et al. |
| 2015/0024355 A1 | 1/2015 | Ghofrani et al. |
| 2015/0027474 A1 | 1/2015 | Zuber et al. |
| 2015/0100441 A1 | 4/2015 | Alarcon et al. |
| 2015/0136124 A1 | 5/2015 | Aronie et al. |
| 2015/0136154 A1 | 5/2015 | Mitrev et al. |
| 2015/0201676 A1 | 7/2015 | Shin |
| 2015/0208725 A1 | 7/2015 | Tsai |
| 2015/0245654 A1 | 9/2015 | Memari et al. |
| 2015/0257445 A1 | 9/2015 | Henry, Jr. et al. |
| 2015/0272211 A1 | 10/2015 | Chung |
| 2016/0150824 A1 | 6/2016 | Memari et al. |
| 2016/0205998 A1 | 7/2016 | Matsumoto et al. |
| 2016/0270437 A1 | 9/2016 | Nappi |
| 2016/0286861 A1 | 10/2016 | Liu |

(56) References Cited

U.S. PATENT DOCUMENTS

| | | |
|---|---|---|
| 2016/0302488 A1 | 10/2016 | Fernando et al. |
| 2016/0031032 A1 | 11/2016 | Malgat et al. |
| 2016/0331032 A1 | 11/2016 | Malgat et al. |
| 2016/0345629 A1 | 12/2016 | Mironov |
| 2016/0366946 A1 | 12/2016 | Murison et al. |
| 2016/0374402 A1 | 12/2016 | Fernando et al. |
| 2017/0006916 A1 | 1/2017 | Liu |
| 2017/0027229 A1 | 2/2017 | Cameron |
| 2017/0027234 A1 | 2/2017 | Farine et al. |
| 2017/0042243 A1 | 2/2017 | Plojoux et al. |
| 2017/0042251 A1 | 2/2017 | Yamada et al. |
| 2017/0055580 A1 | 3/2017 | Blandino et al. |
| 2017/0065002 A1 | 3/2017 | Fernando et al. |
| 2017/0071251 A1 | 3/2017 | Goch |
| 2017/0095006 A1 | 4/2017 | Egoyants et al. |
| 2017/0150757 A1 | 6/2017 | Worm et al. |
| 2017/0164659 A1 | 6/2017 | Schneider et al. |
| 2017/0172214 A1 | 6/2017 | Li et al. |
| 2017/0172215 A1* | 6/2017 | Li .......................... H05B 3/42 |
| 2017/0188634 A1 | 7/2017 | Plojoux et al. |
| 2017/0238596 A1 | 8/2017 | Matsumoto et al. |
| 2018/0177234 A1 | 6/2018 | Lee |
| 2018/0206556 A1 | 7/2018 | Thorens et al. |
| 2018/0235283 A1 | 8/2018 | Zuber et al. |
| 2019/0014826 A1 | 1/2019 | Thorens et al. |
| 2019/0075849 A1 | 3/2019 | Hawes |
| 2019/0320719 A1 | 10/2019 | Liu et al. |
| 2019/0364975 A1 | 12/2019 | Fernando et al. |
| 2020/0006950 A1 | 1/2020 | Holzherr |
| 2020/0120983 A1 | 4/2020 | Chen |
| 2020/0232766 A1 | 7/2020 | Flick |
| 2020/0305508 A1 | 10/2020 | Talon |
| 2020/0352224 A1 | 11/2020 | Plojoux et al. |
| 2020/0413495 A1 | 12/2020 | Schneider et al. |
| 2021/0000182 A1 | 1/2021 | Ruscio et al. |
| 2021/0120875 A1 | 4/2021 | Mironov |

FOREIGN PATENT DOCUMENTS

| | | | |
|---|---|---|---|
| CN | 1102964 | A | 5/1995 |
| CN | 1209731 | A | 3/1999 |
| CN | 1973706 | A | 6/2007 |
| CN | 101043827 | A | 9/2007 |
| CN | 101444335 | A | 6/2009 |
| CN | 102006790 | A | 4/2011 |
| CN | 102438470 | A | 5/2012 |
| CN | 202407082 | U | 9/2012 |
| CN | 202774134 | U | 3/2013 |
| CN | 103096741 | A | 5/2013 |
| CN | 103281920 | A | 9/2013 |
| CN | 103338665 | A | 10/2013 |
| CN | 203457802 | U | 3/2014 |
| CN | 103859606 | A | 6/2014 |
| CN | 203633505 | U | 6/2014 |
| CN | 103929988 | A | 7/2014 |
| CN | 203689071 | U | 7/2014 |
| CN | 103974640 | A | 8/2014 |
| CN | 103997921 | A | 8/2014 |
| CN | 103997922 | A | 8/2014 |
| CN | 203789137 | U | 8/2014 |
| CN | 104023568 | A | 9/2014 |
| CN | 104023574 | A | 9/2014 |
| CN | 104039183 | A | 9/2014 |
| CN | 104095295 | A | 10/2014 |
| CN | 104106842 | A | 10/2014 |
| CN | 203943078 | U | 11/2014 |
| CN | 204070570 | U | 1/2015 |
| CN | 204146338 | U | 2/2015 |
| CN | 104382237 | A | 3/2015 |
| CN | 104470387 | A | 3/2015 |
| CN | 104489933 | A | 4/2015 |
| CN | 104544559 | A | 4/2015 |
| CN | 204317494 | U | 5/2015 |
| CN | 204317504 | U | 5/2015 |
| CN | 104754964 | A | 7/2015 |
| CN | 104770878 | A | 7/2015 |
| CN | 104812260 | A | 7/2015 |
| CN | 204444239 | U | 7/2015 |
| CN | 204763414 | U | 11/2015 |
| CN | 105163610 | A | 12/2015 |
| CN | 105208882 | A | 12/2015 |
| CN | 105208884 | A | 12/2015 |
| CN | 105341993 | A | 2/2016 |
| CN | 105357994 | A | 2/2016 |
| CN | 205018293 | U | 2/2016 |
| CN | 105361250 | A | 3/2016 |
| CN | 105453598 | A | 3/2016 |
| CN | 205180371 | U | 4/2016 |
| CN | 205197003 | U | 5/2016 |
| CN | 205337598 | U | 6/2016 |
| CN | 105747281 | A | 7/2016 |
| CN | 105831812 | A | 8/2016 |
| CN | 105876869 | A | 8/2016 |
| CN | 205512358 | U | 8/2016 |
| CN | 205597118 | U | 9/2016 |
| CN | 106037014 | A | 10/2016 |
| CN | 205648910 | U | 10/2016 |
| CN | 106102492 | A | 11/2016 |
| CN | 106132217 | A | 11/2016 |
| CN | 106163307 | A | 11/2016 |
| CN | 205728067 | U | 11/2016 |
| CN | 106174699 | A | 12/2016 |
| CN | 106231934 | A | 12/2016 |
| CN | 106413439 | A | 2/2017 |
| CN | 106413444 | A | 2/2017 |
| CN | 106455708 | A | 2/2017 |
| CN | 106455714 | A | 2/2017 |
| CN | 106455716 | A | 2/2017 |
| CN | 106473233 | A | 3/2017 |
| CN | 106901404 | A | 6/2017 |
| DE | 3302518 | A1 | 7/1984 |
| EA | 012169 | B1 | 8/2009 |
| EA | 026076 | B1 | 2/2017 |
| EP | 1 119 267 | B1 | 7/2004 |
| EP | 2113178 | A1 | 11/2009 |
| EP | 2 201 850 | A1 | 6/2010 |
| EP | 2253233 | A1 | 11/2010 |
| EP | 2316286 | A1 | 5/2011 |
| EP | 2 531 053 | B1 | 9/2015 |
| EP | 3 098 738 | A1 | 11/2016 |
| EP | 2 432 339 | B1 | 3/2017 |
| EP | 3 179 828 | A1 | 6/2017 |
| EP | 3 275 319 | B1 | 8/2020 |
| GB | 2542018 | A | 3/2017 |
| GN | 205597118 | U | 9/2016 |
| GN | 105342011 | B | 6/2018 |
| JP | 3-232481 | A | 10/1991 |
| JP | 7-184627 | A | 7/1995 |
| JP | 11-164679 | A | 6/1999 |
| JP | 3645921 | B2 | 5/2005 |
| JP | 2006-320286 | A | 11/2006 |
| JP | 4278306 | B2 | 6/2009 |
| JP | 2010-178730 | A | 8/2010 |
| JP | 2010-526553 | A | 8/2010 |
| JP | 2011-87569 | A | 5/2011 |
| JP | 2011-518567 | A | 6/2011 |
| JP | 4739433 | B2 | 8/2011 |
| JP | 2012-527222 | A | 11/2012 |
| JP | 2014-500017 | A | 1/2014 |
| JP | 2014-521419 | A | 8/2014 |
| JP | 2014-525237 | A | 9/2014 |
| JP | 2014-533513 | A | 12/2014 |
| JP | 2014-534813 | A | 12/2014 |
| JP | 2015-503916 | A | 2/2015 |
| JP | 2015-506170 | A | 3/2015 |
| JP | 2015-507477 | A | 3/2015 |
| JP | 2015-508996 | A | 3/2015 |
| JP | 2015-524261 | A | 8/2015 |
| JP | 2015-180214 | A | 10/2015 |
| JP | 2015-529458 | A | 10/2015 |
| JP | 2015-204833 | A | 11/2015 |
| JP | 2016-528910 | A | 9/2016 |
| JP | 3207506 | U | 11/2016 |
| JP | 2017-51189 | A | 3/2017 |

(56) References Cited

FOREIGN PATENT DOCUMENTS

| | | |
|---|---|---|
| JP | 2017-70297 A | 4/2017 |
| JP | 2017-514463 A | 6/2017 |
| KR | 10-0304044 B1 | 11/2001 |
| KR | 10-0636287 B1 | 10/2006 |
| KR | 10-0806461 B1 | 2/2008 |
| KR | 10-0965099 B1 | 6/2010 |
| KR | 10-1001077 B1 | 12/2010 |
| KR | 10-2011-0096548 A | 8/2011 |
| KR | 20-2011-0009632 U | 10/2011 |
| KR | 10-1098112 B1 | 12/2011 |
| KR | 10-2012-0027029 A | 3/2012 |
| KR | 10-2012-0101637 A | 9/2012 |
| KR | 10-1184499 B1 | 9/2012 |
| KR | 10-2012-0109634 A | 10/2012 |
| KR | 10-2012-0114333 A | 10/2012 |
| KR | 10-2012-0121314 A | 11/2012 |
| KR | 10-2013-0027909 A | 3/2013 |
| KR | 20-0466757 Y1 | 5/2013 |
| KR | 10-2013-0081238 A | 7/2013 |
| KR | 10-2013-0139296 A | 12/2013 |
| KR | 10-2014-0015774 A | 2/2014 |
| KR | 10-1383577 B1 | 4/2014 |
| KR | 10-2014-0068203 A | 6/2014 |
| KR | 10-2014-0092312 A | 7/2014 |
| KR | 10-2014-0116055 A | 10/2014 |
| KR | 10-2014-0118983 A | 10/2014 |
| KR | 10-2014-0119072 A | 10/2014 |
| KR | 10-2014-0135774 A | 11/2014 |
| KR | 10-2015-0030409 A | 3/2015 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-2015-0099704 A | 9/2015 |
| KR | 10-2015-0099771 A | 9/2015 |
| KR | 10-2016-0009678 A | 1/2016 |
| KR | 10-2016-0012110 A | 2/2016 |
| KR | 10-2016-0012329 A | 2/2016 |
| KR | 10-2016-0015144 A | 2/2016 |
| KR | 10-2016-0040643 A | 4/2016 |
| KR | 10-1609715 B1 | 4/2016 |
| KR | 10-2016-0052607 A | 5/2016 |
| KR | 10-2016-0060006 A | 5/2016 |
| KR | 10-1619032 B1 | 5/2016 |
| KR | 20-2016-0001476 U | 5/2016 |
| KR | 10-2016-0088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 10-1656061 A | 9/2016 |
| KR | 10-2016-0114743 A | 10/2016 |
| KR | 10-2016-0124091 A | 10/2016 |
| KR | 10-1667124 B1 | 10/2016 |
| KR | 10-1668175 B1 | 10/2016 |
| KR | 10-2016-0129024 A | 11/2016 |
| KR | 10-2016-0131035 A | 11/2016 |
| KR | 10-2016-0133665 A | 11/2016 |
| KR | 10-2016-0137627 A | 11/2016 |
| KR | 10-1679489 B1 | 11/2016 |
| KR | 10-2016-0140608 A | 12/2016 |
| KR | 10-2016-0142896 A | 12/2016 |
| KR | 10-2016-0147253 A | 12/2016 |
| KR | 10-1690389 B1 | 12/2016 |
| KR | 10-2017-0006282 A | 1/2017 |
| KR | 10-2017-0007262 A | 1/2017 |
| KR | 10-2017-0044158 A | 4/2017 |
| KR | 10-2017-0071486 A | 6/2017 |
| KR | 10-2017-0074898 A | 6/2017 |
| KR | 10-1740160 B1 | 6/2017 |
| RU | 2302806 C2 | 7/2007 |
| RU | 2425608 C2 | 8/2011 |
| RU | 2 531 890 C2 | 10/2014 |
| RU | 2564600 C1 | 10/2015 |
| RU | 2014 125 232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 053 C2 | 11/2016 |
| RU | 2 602 962 C2 | 11/2016 |
| RU | 2 603 559 C2 | 11/2016 |
| RU | 2 604 012 C2 | 12/2016 |
| RU | 2604012 C2 | 12/2016 |
| WO | 94/06314 A1 | 3/1994 |
| WO | 98/23171 A1 | 6/1998 |
| WO | 00/27232 A1 | 5/2000 |
| WO | 2010/133342 A1 | 11/2010 |
| WO | 2011/028372 A1 | 3/2011 |
| WO | 2011/050964 A1 | 5/2011 |
| WO | 2011/095781 A1 | 8/2011 |
| WO | 2012/072264 A1 | 6/2012 |
| WO | 2012/123702 A1 | 9/2012 |
| WO | 2013/034458 A1 | 3/2013 |
| WO | 2013/060743 A2 | 5/2013 |
| WO | 2013/076098 A2 | 5/2013 |
| WO | 2013/098395 A1 | 7/2013 |
| WO | 2013/098398 A3 | 7/2013 |
| WO | 2013/098409 A1 | 7/2013 |
| WO | 2013/102609 A2 | 7/2013 |
| WO | 2013/102612 A2 | 7/2013 |
| WO | 2013102609 A2 | 7/2013 |
| WO | 2013/120565 A3 | 8/2013 |
| WO | 2013/126777 A2 | 8/2013 |
| WO | 2013/137084 A1 | 9/2013 |
| WO | 2013/171217 A1 | 11/2013 |
| WO | 2013/190036 A1 | 12/2013 |
| WO | 2014/029880 A2 | 2/2014 |
| WO | 2015/046386 A1 | 4/2015 |
| WO | 2015/088744 A1 | 6/2015 |
| WO | 2015/128665 A1 | 9/2015 |
| WO | WO-2015155289 A1 * | 10/2015 ............ A24F 40/46 |
| WO | 2015/165813 A1 | 11/2015 |
| WO | 2015/177044 A1 | 11/2015 |
| WO | 2015/197627 A1 | 12/2015 |
| WO | 2016/059073 A1 | 4/2016 |
| WO | 2016/075028 A1 | 5/2016 |
| WO | 2016/076147 A1 | 5/2016 |
| WO | 2016/107766 A1 | 7/2016 |
| WO | 2016/124550 A1 | 8/2016 |
| WO | 2016/124552 A1 | 8/2016 |
| WO | 2016/150019 A1 | 9/2016 |
| WO | 2016/156103 A1 | 10/2016 |
| WO | 2016/156219 A1 | 10/2016 |
| WO | 2016/159013 A1 | 10/2016 |
| WO | 2016/166064 A1 | 10/2016 |
| WO | 2016/178377 A1 | 11/2016 |
| WO | 2017/029088 A1 | 2/2017 |
| WO | 2017/029089 A1 | 2/2017 |
| WO | 2017/037457 A1 | 3/2017 |
| WO | 2017/042297 A1 | 3/2017 |
| WO | 2017/075759 A1 | 5/2017 |
| WO | 2017/139963 A1 | 8/2017 |
| WO | 2018/050449 A1 | 3/2018 |
| WO | 2018/189195 A1 | 10/2018 |
| WO | 2019/020826 A1 | 1/2019 |
| WO | 2019/030172 A1 | 2/2019 |
| WO | 2019/095268 A1 | 5/2019 |

OTHER PUBLICATIONS

Office Action dated Dec. 11, 2019 in Korean Application No. 10-2018-0010841.
Office Action dated Dec. 19, 2019 in Korean Application No. 10-2018-0090910.
Office Action dated Jan. 3, 2020 in Korean Application No. 10-2018-0012456.
Office Action dated Jan. 3, 2020 in Korean Application No. 10-2017-0084389.
Office Action dated Jan. 3, 2020 in Korean Application No. 10-2017-0084386.
Office Action dated Jan. 3, 2020 in Korean Application No. 10-2018-0018693.

(56) References Cited

OTHER PUBLICATIONS

Office Action dated Jan. 8, 2020 in Korean Application No. 10-2017-0128293.
Office Action dated Jan. 8, 2020 in Korean Application No. 10-2017-0119664.
Office Action dated Jan. 16, 2020 in Korean Application No. 10-2017-0084388.
Office Action dated Jan. 16, 2020 in Korean Application No. 10-2017-0084387.
Office Action dated Feb. 11, 2020 in Korean Application No. 10-2018-0010834.
Office Action dated Feb. 11, 2020 in Korean Application No. 10-2018-0010835.
Office Action dated Feb. 13, 2020 in Korean Application No. 10-2018-0010837.
Office Action dated Feb. 18, 2020 in Russian Application No. 2019121813.
Office Action dated Aug. 7, 2019 for Korean Patent Application No. 10-2018-0067035, and its English translation provided by Applicants foreign counsel.
Office Action dated Jun. 27, 2019 for Korean Patent Application No. 10-2018-0063759, and its English translation provided by Applicants foreign counsel.
Office Action dated Jul. 2, 2019 for Korean Patent Application No. 10-2019-0018815, and its English translation provided by Applicants foreign counsel.
Office Action dated Jul. 3, 2019 for Korean Patent Application No. 10-2019-0017391, and its English translation provided by Applicants foreign counsel.
International Preliminary Report on Patentability (Chapter I) dated Jun. 18, 2019 for PCT/KR2017/012486 and its English translation from WIPO.
Written Opinion of the International Searching Authority for PCT/KR2017/012486 dated May 29, 2018 and its English translation by Google Translate (now published as WO 2018/110834).
Partial supplementary European search report dated Aug. 3, 2020 in Application No. 17880867.1.
Extended European search report dated Nov. 4, 2020 by the European Patent Office in Application No. 17880867.1.
Office Action dated Oct. 29, 2020 by the Korean Patent Office in Application No. 10-2018-0010837.
Office Action dated Nov. 4, 2020 by the Japanese Patent Office in Application No. 2019-554453.
Office Action dated Nov. 4, 2020 by the Japanese Patent Office in Application No. 2020-128346.
Decision on Grant dated Nov. 26, 2020 by the Russian Federal Service For Intellectual Property Patent Application No. 2020124607.
Office Action dated Nov. 26, 2020 by Russian Federal Service For Intellectual Property Office Patent Application No. 2020124609.
Decision on Grant dated Oct. 26, 2020 by Russian Federal Service For Intellectual Property in Application No. 2020124610.
Office Action dated Jun. 29, 2020 by the Korean Patent Office in Application No. 10-2018-0010836.
Office Action dated Nov. 14, 2019 in Korean Application No. 10-2017-0084385.
Office Action dated Nov. 14, 2019 in Korean Application No. 10-2017-0147605.
International Search Report dated Jul. 24, 2018 in International Application No. PCT/KR2018/003691.
Office Action dated Jul. 2, 2019 in Korean Application No. 10-2019-0018815.
Office Action dated Jul. 3, 2019 in Korean Application No. 10-2019-0017391.
International Search Report dated Oct. 29, 2018 in International Application No. PCT/KR2018/004181.
International Search Report dated Sep. 6, 2018 in International Application No. PCT/KR2018/004179.
International Search Report dated Nov. 6, 2018 in International Application No. PCT/KR2018/004178.
International Search Report dated Sep. 6, 2018 in International Application No. PCT/KR2018/004176.
International Search Report dated Sep. 7, 2018 in International Application No. PCT/KR2018/004172.
International Search Report dated Sep. 7, 2018 in International Application No. PCT/KR2018/004171.
International Search Report dated Nov. 6, 2018 in International Application No. PCT/KR2018/004130.
International Search Report dated Nov. 14, 2018 in International Application No. PCT/KR2018/004118.
International Search Report dated May 29, 2018 in International Application No. PCT/KR2017/012486.
Extended European Search Report dated Dec. 11, 2020 in European Application No. 20188967.2.
Extended European Search Report dated Dec. 16, 2020 in European Application No. 20188985.4.
Office Action dated Dec. 30, 2020 in Russian Application No. 2020124651.
Office Action dated Dec. 28, 2020 in Russian Application No. 2020124652.
Office Action dated Dec. 11, 2020 in Russian Application No. 2020124653.
Office Action dated Jan. 22, 2021 in Russian Application No. 2020124657.
Office Action dated Jan. 22, 2021 in Russian Application No. 2020124658.
Extended European Search Report dated Dec. 18, 2020 in European Application No. 18775504.6.
Office Action dated Jan. 19, 2021 in Japanese Application No. 2019-553569.
Extended European Search Report dated Jan. 14, 2021 in European Application No. 18784738.9.
Extended European Search Report dated Dec. 10, 2020 in European Application No. 20188932.6.
Office Action dated Jan. 12, 2021 in Japanese Application No. 2019-555201.
Office Action dated Jan. 12, 2021 in Japanese Application No. 2019-555169.
Office Action dated Jan. 5, 2021 in Japanese Application No. 2019-558557.
Extended European Search Report dated Nov. 19, 2020 in European Application No. 20188792.4.
Office Action dated Dec. 1, 2020 in Japanese Application No. 2020-501188.
Extended European Search Report dated Dec. 18, 2020 in European Application No. 20188926.8.
Office Action dated Jan. 19, 2021 in Japanese Application No. 2020-501514.
Office Action dated Sep. 24, 2020 in Korean Application No. 10-2018-0012456.
Office Action dated May 28, 2020 in Korean Application No. 10-2017-0147605.
Extended European Search Report dated Jan. 14, 2021 in European Application No. 18783776.0.
Extended European Search Report dated Jan. 25, 2021 in European Application No. 18785166.2.
Extended European Search Report dated Jan. 29, 2021 in European Application No. 18784464.2.
Extended European Search Report dated Mar. 15, 2021 in European Application No. 18785061.5.
Extended European Search Report dated Mar. 19, 2021 in European Application No. 18784164.8.
Extended European Search Report dated Mar. 24, 2021 in European Application No. 18784268.7.
Extended European Search Report dated Mar. 25, 2021 in European Application No. 18784370.1.
Extended European Search Report dated Mar. 25, 2021 in European Application No. 18784841.1.
Office Action dated Feb. 24, 2021 in Japanese Application No. 2019-555168.
Office Action dated Feb. 24, 2021 in Japanese Application No. 2019-555203.

(56) References Cited

OTHER PUBLICATIONS

Office Action dated Feb. 24, 2021 in Japanese Application No. 2019-555204.
Office Action dated Feb. 4, 2021 in Russian Application No. 2020124609.
Office Action dated Feb. 9, 2021 in Japanese Application No. 2019-555184.
Office Action dated Jan. 26, 2021 in Japanese Application No. 2020-501521.
Office Action dated Mar. 2, 2021 in Japanese Application No. 2019-555170.
Office Action dated Mar. 2, 2021 in Japanese Application No. 2019-555182.
Office Action dated Mar. 30, 2021 in Japanese Application No. 2020-501377.
Office Action dated Jan. 19, 2021 in Indonesian Application No. P00201906007.
Communication dated Apr. 4, 2019 by the Korean Patent Office in Korean Application No. 10-2019-0019194.
Communication dated Apr. 4, 2019 by the Korean Patent Office in Korean Application No. 10-2019-0019195.
Communication dated Apr. 5, 2019 by the Korean Patent Office in Korean Application No. 10-2019-0027638.
Communication dated Apr. 25, 2019 by the Korean Patent Office in Korean Application No. 10-2019-0033784.
Communication dated Apr. 9, 2021 by the Korean Patent Office in Korean Application No. 10-2020-0116256.
Communication dated Jul. 22, 2021 by the Korean Patent Office in Korean Application No. 10-2021-0051359.
Communication dated May 5, 2021 by the Canadian Patent Office in Canadian Application No. 3,047,236.
Extended European Search Report dated Jan. 15, 2021 in European Application No. 20188949.0.
Communication dated Jun. 10, 2021 by the Russian Patent Office in Russian Application No. 2020124657.
Communication dated Jun. 10, 2021 by the Russian Patent Office in Russian Application No. 2020124658.
Communication dated Jun. 29, 2021 by the Chinese Patent Office in Chinese Application No. 201880022072.2.
Extended European Search Report dated Apr. 1, 2021 in European Application No. 18805933.1.
Extended European Search Report dated Jun. 16, 2021 in European Application No. 18853434.1.
Extended European Search Report dated Jul. 1, 2021 in European Application No. 18854661.8.
Extended European Search Report dated Jun. 14, 2021 in European Application No. 18842951.8.
International Search Report dated Nov. 6, 2018 in International Application No. PCT/KR2018/004129.
International Search Report dated Aug. 29, 2018 in International Application No. PCT/KR2018/005945.
International Search Report dated Nov. 30, 2018 in International Application No. PCT/KR2018/006702.
International Search Report dated Dec. 4, 2018 in International Application No. PCT/KR2018/006747.
International Search Report dated Nov. 26, 2018 in International Application No. PCT/KR2018/009094.
International Search Report dated Feb. 28, 2019 in International Application No. PCT/KR2018/009100.
Communication dated Aug. 16, 2021 by the Chinese Patent Office in Chinese Application No. 201880024006.9.
Communication dated Aug. 26, 2021 by the Chinese Patent Office in Chinese Application No. 201880024107.6.
Communication dated Aug. 4, 2021 by the Chinese Patent Office in Chinese Application No. 201880024289.7.
Communication dated Jul. 16, 2021 by the Chinese Patent Office in Chinese Application No. 201880024367.3.
Communication dated Jul. 19, 2021 by the Chinese Patent Office in Chinese Application No. 201880024070.7.
Communication dated Jul. 26, 2021 by the Chinese Patent Office in Chinese Application No. 201880024059.0.
Communication dated Jul. 27, 2021 by the Chinese Patent Office in Chinese Application No. 201780084891.5.
Communication dated Sep. 17, 2021 by the Chinese Patent Office in Chinese Application No. 201880030699.2.
Extended European Search Report issued Oct. 27, 2021 in European Application No. 18844735.3.
Office Action dated Oct. 28, 2021 in Chinese Application No. 201880046418.2.
Office Action dated Sep. 24, 2021 in Chinese Application No. 201880024010.5.
Office Action dated Sep. 29, 2021 in Chinese Application No. 201880024276.X.
Office Action dated Sep. 29, 2021 in Chinese Application No. 201880024311.8.
Office Action dated Nov. 25, 2021 in Chinese Application No. 201880047174.X.
Office Action dated Dec. 1, 2021 in Chinese Application No. 201880046367.3.

* cited by examiner

AEROSOL GENERATING DEVICE PROVIDED WITH ROTARY HEATER

CROSS REFERENCE TO RELATED APPLICATIONS

This application is a National Stage of International Application No. PCT/KR2018/004181 filed Apr. 10, 2018, claiming priority based on Korean Patent Application No. 10-2017-0046938 filed Apr. 11, 2017, Korean Patent Application No. 10-2017-0077586 filed Jun. 19, 2017, and Korean Patent Application No. 10-2017-0128293 filed Sep. 29, 2017.

TECHNICAL FIELD

Embodiments relate to an aerosol generating device provided with a rotary heater, and more particularly, to an aerosol generating device in which a heater rotates before a cigarette is separated to conveniently separate the cigarette and the heater and discharge a residue to the outside of the aerosol generating device along with the cigarette.

BACKGROUND ART

Recently, the demand for a method of generating aerosol by heating an aerosol generating material in a cigarette has increased, and thus, research into a heated cigarette or a heated aerosol generating device has been actively conducted.

When an aerosol generating device provided with a heater that heats a cigarette by using electricity is used, the cigarette that generates a smoking gas by being heated by the heater may be separated from the aerosol generating device and may be discarded, and then a new cigarette may be inserted into the aerosol generating device.

Korean Patent Registration No. 10-1667124 relates to an aerosol generating device that generates a smoking gas by heating a cigarette, and describes a structure of a holder that assists an operation of inserting the cigarette into the aerosol generating device or an operation of separating the cigarette from the aerosol generating device.

When a user uses an aerosol generating device having such a structure, the user inserts a cigarette into a holder extracted from the aerosol generating device to the outside and pushes the holder and the cigarette into the aerosol generating device for smoking, and after smoking, pulls the holder out of the aerosol generating device and then removes the cigarette from the holder.

In the aerosol generating device including the holder configured as above, because the holder simply guides an operation of inserting and separating the cigarette into and from the holder, a residue generated from the cigarette heated during smoking remains on elements such as the heater and an internal space of the aerosol generating device, thereby making it difficult to keep the aerosol generating device clean.

When the user separates the cigarette from the aerosol generating device, the user holds the cigarette inserted into the holder in his/her hand and pulls the cigarette out of the holder to remove the cigarette from the aerosol generating device, and in this case, a tobacco component attached to contact surfaces of the cigarette and the heater is not separated and remains on the heater even during separation of the cigarette by the user. The tobacco component generated from the cigarette is attached to the contact surfaces between the cigarette and the heater, and because the tobacco component attached to the heater is condensed due to heat of the heater to further increase an adhesive force, a degree of cleanliness of the internal space of the aerosol generating device and the heater decreases as the time during which the aerosol generating device is used increases.

DESCRIPTION OF EMBODIMENTS

Technical Problem

Embodiments provide an aerosol generating method and device. Also, embodiments provide a computer-readable recording medium having embodied thereon a program for executing the aerosol generating method in a computer.

Also, embodiments provide an aerosol generating device for conveniently separating a cigarette.

Also, embodiments provide an aerosol generating device for removing a material attached to a heater.

Technical problems to be solved by embodiments are not limited to the above-described technical problems and there may be other technical problems.

Solution to Problem

Embodiments may implement an aerosol generating device provided with a rotary heater.

An aerosol generating device provided with a rotary heater according to an embodiment includes: a casing having a hollow shape and comprising a path in which a cigarette is accommodated; a rotating member rotatably coupled to the casing; and a heater that has an end portion located inside the path to be inserted into the cigarette accommodated in the path, is connected to the rotating member to rotate along with the rotating member, and heats the cigarette when electricity is applied to the heater.

The rotating member may be coupled to the casing to rotate about a central axis in a longitudinal direction of the path.

The heater may rotate about the central axis in the longitudinal direction of the path.

The aerosol generating device may further include a connector connecting the rotating member to the heater and rotating along with the rotating member and the heater.

The aerosol generating device may further include a protruding portion protruding from any one of the connector and the rotating member, and a groove portion formed in the other of the connector and the rotating member so that the protruding portion is inserted into the groove portion, wherein the casing further comprises an intermediate container having a guide hole allowing the protruding portion to pass therethrough and extending in a circumferential direction about a center of rotation of the rotating member to provide a movement path for the protruding portion while the rotating member rotates.

The intermediate container may further include a rotation limiter configured to limit movement of the protruding portion.

The connector may have a through-hole through which the end portion of the heater passes, and may include a coupling protrusion protruding from one of the heater and the through-hole and a coupling groove formed in the other of the heater and the through-hole so that the coupling protrusion is inserted into the coupling groove.

The aerosol generating device may further include a pressing member provided in a path in which the protruding portion moves and configured to apply an elastic force with respect to movement of the protruding portion.

The casing may further include an inner container having a hollow shape, comprising the path in which the cigarette is accommodated, and located inside the intermediate container, and an outer container having a hollow shape and located outside the intermediate container.

The aerosol generating device may further include a cap coupled to an end portion of the inner container and having a hole through which the end portion of the heater passes.

The aerosol generating device may further include a movement protrusion protruding from any one of the rotating member and the casing, and a guide groove portion formed in the other of the rotating member and the casing so that the movement protrusion is inserted into the guide groove portion and extending in a circumferential direction about center of rotation of the rotating member to guide movement of the protruding portion.

An aerosol generating system according to another embodiment includes: a holder configured to generate aerosol by heating a cigarette; and a cradle having an internal space into which the holder is inserted, wherein the holder is inserted into the internal space of the cradle and then is tilted to generate the aerosol.

A cigarette inserted into a holder according to another embodiment includes: a tobacco rod including a plurality of tobacco strands; a first filter segment that is hollow; a cooling structure configured to cool generated aerosol; and a second filter segment.

Advantageous Effects of Disclosure

In an aerosol generating device provided with a rotary heater according to the above embodiments, because a heater first rotates due to the rotation of a rotating member before a cigarette is separated and thus contact surfaces between the heater and the cigarette are separated, the cigarette and the heater may be conveniently separated.

Also, because the heater rotates and thus a state in which a residue is attached to the cigarette is maintained, the residue attached to the cigarette may be easily discharged to the outside of the aerosol generating device along with the cigarette.

BEST MODE

With respect to the terms in the various embodiments of the present disclosure, the general terms which are currently and widely used are selected in consideration of functions of structural elements in the various embodiments of the present disclosure. However, meanings of the terms may be changed according to intention, a judicial precedent, appearance of a new technology, and the like. In addition, in certain cases, a term which is not commonly used may be selected. In such a case, the meaning of the term will be described in detail at the corresponding part in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, embodiments will be described in detail with reference to the drawings. The present disclosure may, however, be embodied in many different forms and should not be construed as limited to the embodiments set forth herein.

MODE OF DISCLOSURE

Figure 1:
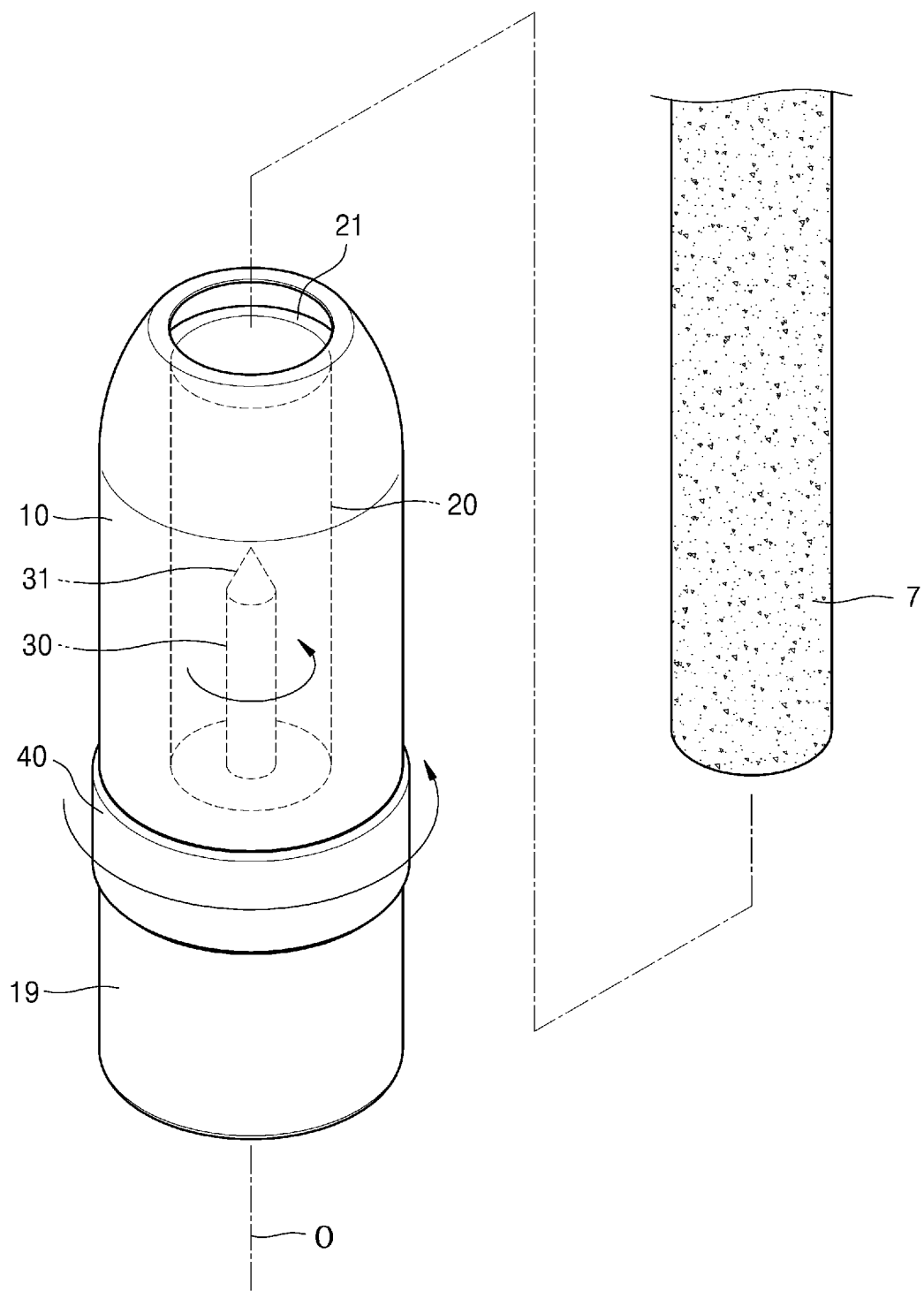
FIG. 1 is a perspective view of an aerosol generating device provided with a rotary heater according to an embodiment.
Figure 2:
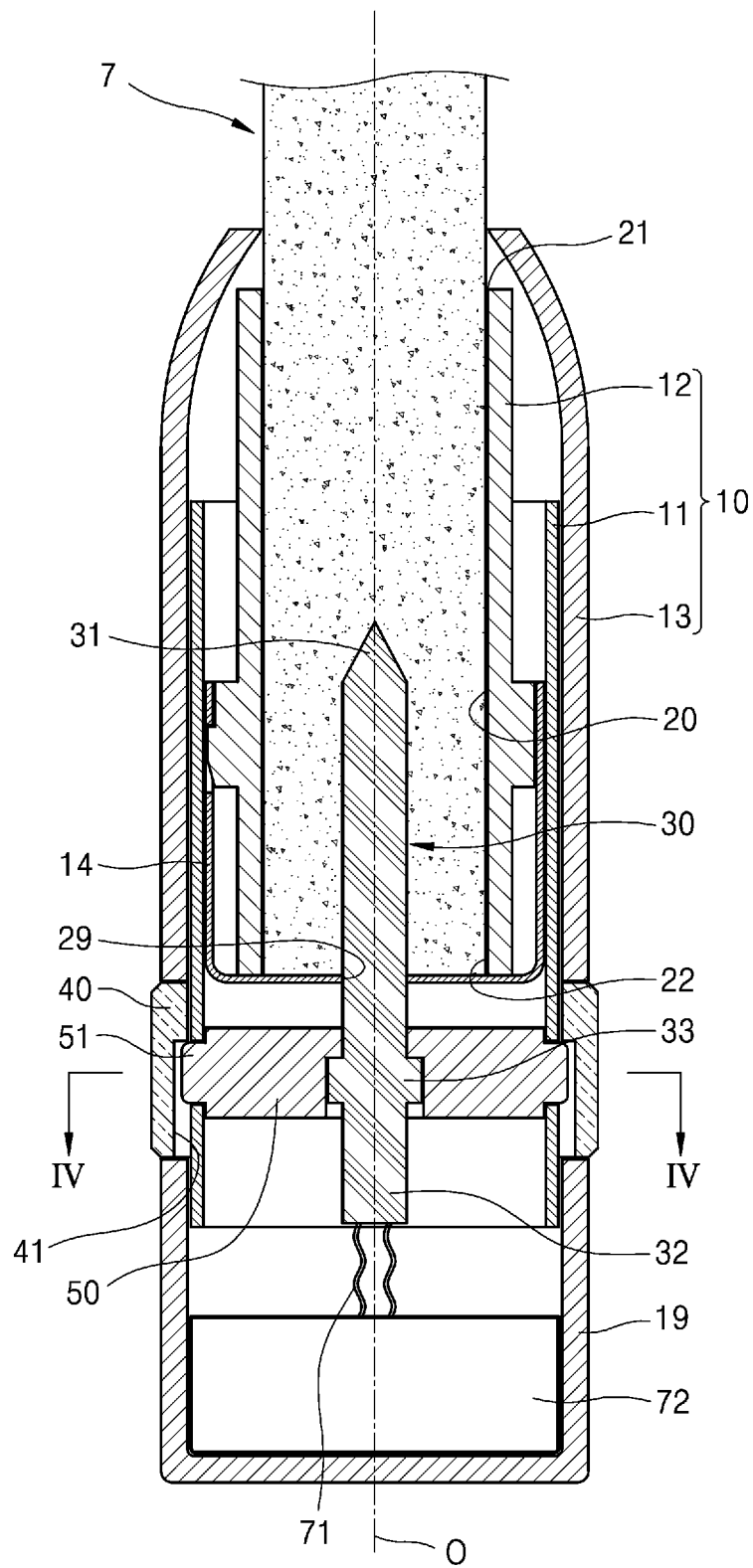
FIG. 2 is a longitudinal-sectional view of the aerosol generating device according to the embodiment of FIG. 1.
Figure 3:
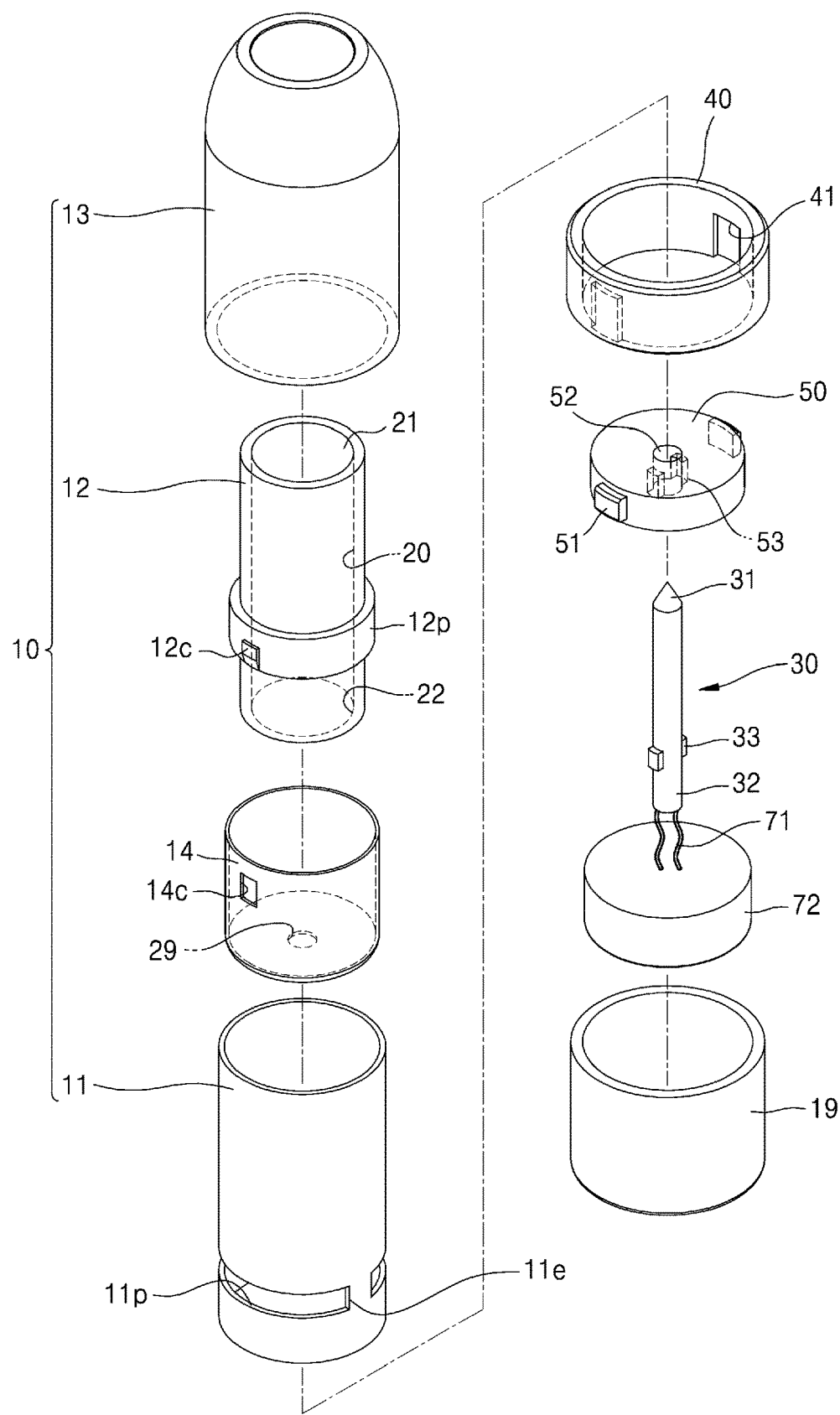
FIG. 3 is an exploded perspective view illustrating a coupling relationship between elements of the aerosol generating device according to the embodiment of FIG. 1.

FIG. 1 is a perspective view of an aerosol generating device provided with a rotary heater according to an embodiment, FIG. 2 is a longitudinal-sectional view of the aerosol generating device according to the embodiment of FIG. 1, and FIG. 3 is an exploded perspective view illustrating a coupling relationship between elements of the aerosol generating device according to the embodiment of FIG. 1.

The aerosol generating device provided with the rotary heater according to the embodiment of FIGS. 1 through 3 includes a casing 10 having a hollow shape and including a path 20 in which a cigarette 7 is accommodated, a rotating member 40 rotatably coupled to the casing 10, and a heater 30 rotating along with the rotating member 40 and heating the cigarette 7.

The casing 10 forms the exterior of the aerosol generating device and accommodates and protects various elements in an internal space thereof. The casing 10 has a hollow cylindrical shape whose inside is empty, and has a front end portion open to the outside so that the cigarette 7 is inserted into the casing 10 through the front end portion.

The casing 10 may be formed of a plastic material having without electric conductivity and heat conductivity, or may be formed of a metal material having a surface coated with a plastic material. Although the casing 10 has a cylindrical shape having a circular cross-section in the embodiment, the embodiment is not limited by a configuration of the casing 10. For example, the casing 10 may have a polygonal cross-sectional shape such as a quadrangular cross-sectional shape.

The path 20 in which the cigarette 7 is accommodated is formed inside the casing 10. The cigarette 7 may have a cylindrical shape, and the path 20 has an inner diameter corresponding to an outer diameter of the cigarette 7.

Referring to FIGS. 2 and 3, the casing 10 includes an inner container 12 having a hollow shape and including the path 20 in which the cigarette 7 is accommodated, an intermediate container 11 having a hollow shape and coupled to an outer surface of the inner container 12, and an outer container 13 coupled to an outer surface of the intermediate container 11.

The inner container 12 includes the path 20 for accommodating the cigarette 7, a first opening 21 open at an end of the path 20 to the outside so that the cigarette 7 is inserted from the outside into the first opening 21, and a second opening 22 open at the other end of the path 20.

The path 20 formed in the inner container 12 has a cylindrical shape corresponding to a shape of the cigarette 7. The embodiment is not limited by a shape of the path 20, and, for example, the path 20 may be formed to have a polygonal cross-sectional shape such as a quadrangular cross-sectional shape.

The inner container 12 includes a flange 12p protruding from the outer surface of the inner container 12 and extending in a circumferential direction about a central axis of the inner container 12, and a coupling protrusion 12c protruding outward from the flange 12p.

A cap 14 having a hole 29 through which a first end portion 31 of the heater 30 passes is coupled to the second opening 22 of the inner container 12. The cap 14 includes a coupling groove 14c with which the coupling protrusion 12c of the inner container 12 is coupled. When the cap 14 is coupled to the inner container 12 to cover the second opening 22 of the inner container 12, the coupling protrusion 12c of the inner container 12 is coupled with the coupling groove 14c of the cap 14 and thus the cap 14 is fixed to the inner container 12.

The embodiment is not limited by a configuration in which the cap 14 and the inner container 12 are independent elements, and, for example, the cap 14 and the inner container 12 may be integrally formed as one element.

The cap 14 contacts an end portion of the cigarette 7 accommodated in the path 20. When a user of the aerosol generating device moves the cigarette 7 along the path 20 by inserting the cigarette 7 into the path 20 and the end portion of the cigarette 7 reaches the cap 14, a sense of touch that the end portion of the cigarette 7 contacts the cap 14 may be transmitted to the user's hand holding the cigarette 7. Accordingly, the user may conveniently mount the cigarette 7 onto the aerosol generating device by a simple action of holding the cigarette 7 in his/her hand and pushing the cigarette 7 into the first opening 21 of the path 20.

The inner container 12 is an innermost container of the casing 10, and provides a movement path of the cigarette 7 so that the cigarette 7 inserted from the outside moves along the path 20 and accommodates the cigarette 7 therein. After the inner container 12, the intermediate container 11, and the outer container 13 are coupled to one another, while the aerosol generating device is used, the inner container 12 does not move relative to the intermediate container 11 and the outer container 13 and is maintained at a fixed position.

The heater 30 for heating the cigarette 7 is provided in the casing 10. The heater 30 is fabricated to have a pin shape or a rod shape and the first end portion 31 of the heater 30 is located inside the path 20 through the hole 29 of the cap 14, and, when the cigarette 7 is accommodated in the casing 10, the first end portion 31 of the heater 30 is inserted into the end portion of the cigarette 7.

A size of the hole 29 formed in the cap 14 may correspond to a thickness of the first end portion 31 of the heater 30. For example, when the first end portion 31 of the heater 30 has a circular cross-sectional shape, the hole 29 has a circular cross-sectional shape, and an inner diameter of the hole 29 corresponds to an outer diameter of the first end portion 31 of the heater 30.

The embodiment is not limited by a size of the inner diameter of the hole 29, and, for example, the inner diameter of the hole 29 may be greater than the outer diameter of the first end portion 31 of the heater 30 and an inner surface of the hole 29 may be spaced apart from an outer surface of the first end portion 31 of the heater 30.

A second end portion 32 of the heater 30 that is opposite to the first end portion 31 is electrically connected to an electricity supplying device 72 located at a rear portion of the casing 10 through an electrical wiring 71. A base 19 surrounding the electricity supplying device 72 is connected to the rear portion of the casing 10. The base 19 may rotatably support the rotating member 40 so that the rotating member 40 may rotate along with the casing 10.

When electricity of the electricity supplying device 72 is supplied to the heater 30 in a state where the cigarette 7 is inserted into the first end portion 31 of the heater 30, the heater 30 is heated and the cigarette 7 is heated accordingly.

The rotating member 40 is exposed to an outside of the casing 10 and rotatably coupled to the casing 10 to rotate about a central axis O in a longitudinal direction of the path 20. When the user holds the rotating member 40 in his/her hand and rotates the rotating member 40, the rotating member 40 rotates about the central axis O, and the heater 30 also rotates about the central axis O along with the rotating member 40.

The rotating member 40 may be formed of a material having low electrical conductivity and low heat conductivity. For example, the rotating member 40 may be formed of a material such as rubber or plastic, or may be formed of a metal material and then an outer surface of the rotating member 40 which is touched by the user's hands may be coated with a material without heat conductivity and electrical conductivity.

The rotating member 40 may be coupled to an outer surface of the casing 10, and may rotate relative to the casing 10. The rotating member 40 has a hollow cylindrical shape whose inside is empty. The rotating member 40 includes a groove portion 41 having a concave shape and formed in an inner surface of the rotating member 40.

A connector 50 is coupled to the inside of the rotating member 40. The connector 50 has a substantially circular plate shape. Because the connector 50 connects the rotating member 40 and the heater 30, the connector 50 may rotate along with the rotating member 40 and the heater 30. The connector 50 includes a protruding portion 51 that protrudes outward. When the connector 50 is located inside the rotating member 40, the protruding portion 51 of the connector 50 is inserted into the groove portion 41 of the rotating member 40, thereby limiting the rotation of the connector 50 relative to the rotating member 40.

The embodiment is not limited by a shape of the connector 50, and, for example, the connector 50 may have a cylindrical shape or a rod shape.

Although a configuration in which the protruding portion 51 is formed on the connector 50 and the groove portion 41 is formed in the rotating member 40 is described in the embodiment, the embodiment is not limited by the configuration, and, for example, a groove portion may be formed in the connector 50 and a protruding portion may be formed on the rotating member 40. Also, the connector 50 and the rotating member 40 may be coupled to each other by using an adhesive, facing screw surfaces, or fastening means such as screws, instead of using a groove portion and a protruding portion.

The protruding portion 51 of the connector 50 is inserted through a guide hole 11p of the intermediate container 11 into the groove portion 41 of the rotating member 40. The guide hole 11p is formed by extending by a pre-determined angle in a circumferential direction about a central axis of the intermediate container 11, that is, the circumferential direction about the center of rotation of the rotating member 40. The intermediate container 11 includes a rotation limiter 11e formed at an end of the guide hole 11p.

The connector 50 has a through-hole 52 through which the first end portion 31 of the heater 30 passes. Also, a coupling groove 53 having a concave shape is formed in an inner wall of the through-hole 52 of the connector 50. A coupling protrusion 33 protruding to have a shape corresponding to the coupling groove 53 is formed on an outer surface of the heater 30.

When the first end portion 31 of the heater 30 passes through the through-hole 52 of the connector 50, the coupling protrusion 33 protruding from the outer surface of the heater 30 is inserted into the coupling groove 53 of the connector 50, and thus the heater 30 is coupled to the connector 50 and the connector 50 and the heater 30 form one body rotating together.

Although only a configuration in which the coupling protrusion 33 is formed on the heater 30 and the coupling groove 53 is formed in the connector 50 is described in the illustrated embodiment, the embodiment is not limited by the configuration, and, for example, a coupling groove may be formed in the heater 30 and a coupling protrusion may be formed on the connector 50. Also, the heater 30 and the connector 50 may be coupled to each other by using an adhesive, facing screw surfaces, or fastening means such as screws, instead of using a coupling protrusion and a coupling groove.

Figure 4:
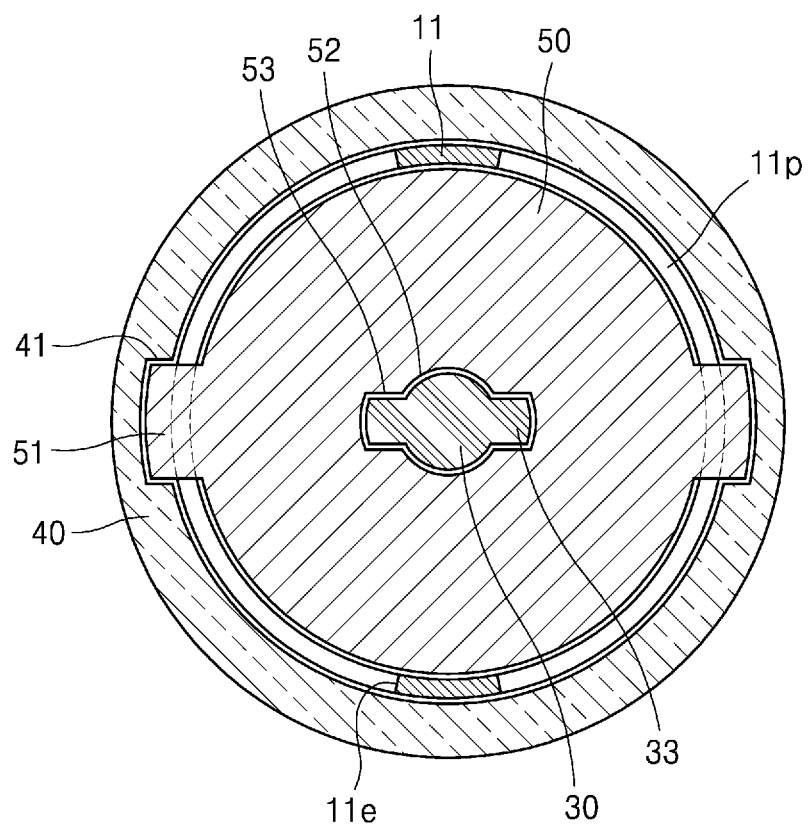
FIG. 4 is a transverse-sectional view taken along line IV-IV of the aerosol generating device of FIG. 2.
Figure 5:
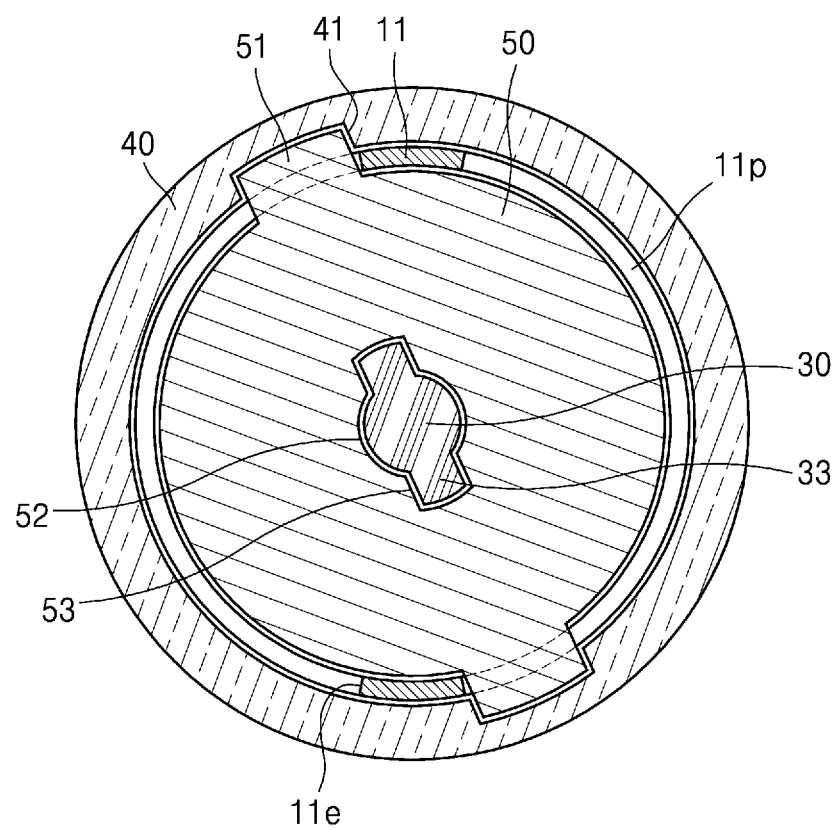
FIG. 5 is a transverse-sectional view illustrating an operating state of the aerosol generating device of FIG. 4.

FIG. 4 is a transverse-sectional view taken along line IV-IV of the aerosol generating device of FIG. 2, and FIG. 5 is a transverse-sectional view illustrating an operating state of the aerosol generating device of FIG. 4.

As the rotating member 40 rotates, the connector 50 and the heater 30 connected to the rotating member 40 rotate along with the rotating member 40. Because the protruding portion 51 of the connector 50 may rotate along the guide hole 11p of the intermediate container 11, the connector 50, the rotating member 40, and the heater 30 may rotate together within a range where the protruding portion 51 may move along the guide hole 11p.

When the rotating member 40 rotates clockwise in a state of FIG. 4, the rotating member 40, the connector 50, and the heater 30 rotate together clockwise to be in a state of FIG. 5. Because the rotation limiter 11e that limits the movement of the protruding portion 51 is located at the end of the guide hole 11p, the rotating member 40, the connector 50, and the heater 30 may rotate together until the protruding portion 51 contacts the rotation limiter 11e.

FIG. 2 is a view illustrating a state where the cigarette 7 is mounted onto the aerosol generating device. In order for the aerosol generating device to perform a tobacco smoke generating function, the cigarette 7 is inserted into a lowermost end of the path 20 of the casing 10 as shown in FIG. 2. A total length of the heater 30 is about 20 mm, and a length of the first end portion 31 of the heater 30 inserted into the cigarette 7 is about 12 mm. Because a rear end portion of the cigarette 7 is inserted into the first end portion 31 of the heater 30 in this state, when electricity is supplied to the heater 30, the heater 30 may heat the cigarette 7 and thus may generate aerosol.

In the aerosol generating device according to the embodiment of FIGS. 1 through 5, the user may easily mount the cigarette 7 onto the aerosol generating device by simply inserting the cigarette 7 into the path 20 of the casing 10 and then pushing the cigarette 7 along the path 20. Also, after using the cigarette 7, the user may separate the cigarette 7 from the aerosol generating device by simply holding an upper end portion of the cigarette 7 protruding from an upper end of the aerosol generating device in his/her hand and pulling the cigarette 7 out of the path 20.

After using the aerosol generating device, the user has to remove the cigarette 7 from the aerosol generating device. When the user rotates the rotating member 40 before the cigarette 7 is removed from the aerosol generating device of FIG. 2, the heater 30 rotates about the central axis O along with the connector 50. While the heater 30 rotates, a position of the cigarette 7 with respect to the casing 10 is not changed and is maintained.

A tobacco material (or a residue) generated from the cigarette 7 while the cigarette 7 is heated by the heater 30 may be condensed and trapped in contact surfaces between the heater 30 and the cigarette 7. When the heater 30 rotates in a state where the first end portion 31 of the heater 30 is inserted into the cigarette 7 as shown in FIG. 2, the contact surfaces between the cigarette 7 and the heater 30 which are attached to each other due to the tobacco material trapped in the contact surfaces between the cigarette 7 and the heater 30 may be easily separated from each other.

When the heater 30 rotates and thus the contact surfaces between the heater 30 and the cigarette 7 are separated from each other, the user may hold the cigarette 7 and may pull the cigarette 7 out of the path 20 of the casing 10, to completely separate the cigarette 7 from the casing 10 of the aerosol generating device.

In a conventional aerosol generating device, because a user separates a cigarette from the conventional aerosol generating device by simply pulling the cigarette from the conventional aerosol generating device, a tobacco material present between the cigarette and a heater is trapped in the heater in many cases.

However, in the aerosol generating device according to the embodiment, before the cigarette 7 is separated from the aerosol generating device, the heater 30 is rotated by rotating the rotating member 40 in a state where the cigarette 7 is maintained at a fixed position with respect to the casing 10.

Because the cigarette 7 is maintained in a fixed state with respect to the casing 10 while the heater 30 rotates and a position of the cigarette 7 with respect to the casing 10 is not changed, the contact surfaces between the cigarette 7 and the heater 30 attached to each other due to the tobacco material may be easily separated. Also, in this process, a state where the residue present between the cigarette 7 and the heater 30 is transferred to the cigarette 7 is maintained.

Because the heater 30 and the cigarette 7 are first separated from each other through the above operation, and then the user may hold the cigarette 7 and may separate the cigarette 7 from the aerosol generating device, the residue transferred to the cigarette 7 may be easily discharged to the outside of the aerosol generating device along with the cigarette 7.

Figure 6:
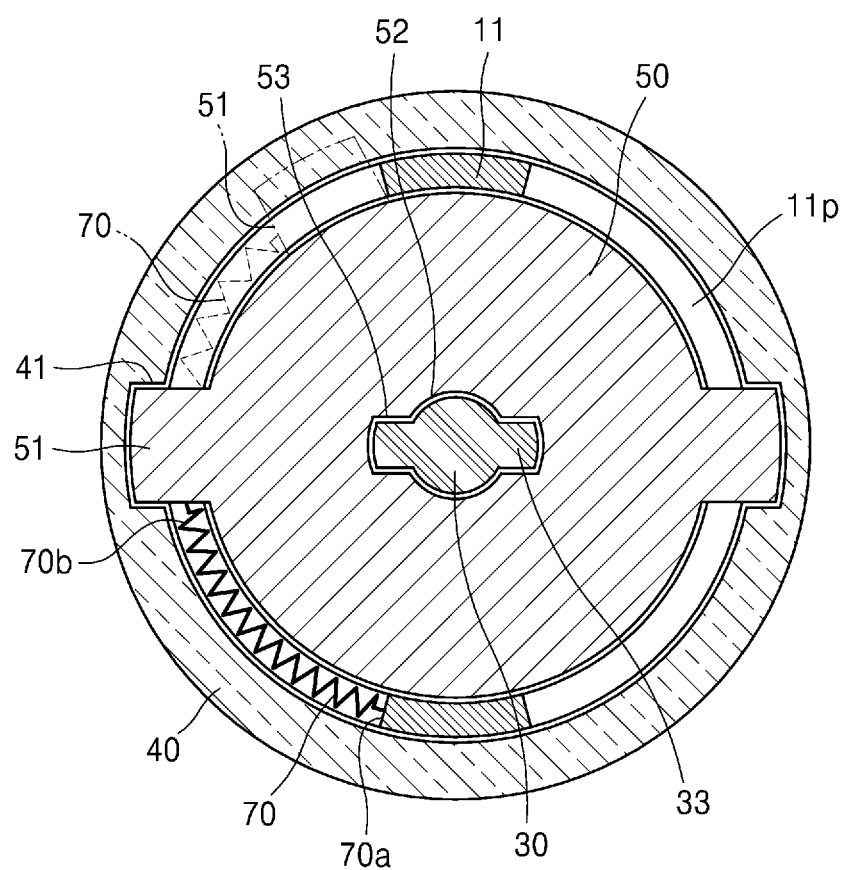
FIG. 6 is a transverse-sectional view of an aerosol generating device according to another embodiment.

FIG. 6 is a transverse-sectional view of an aerosol generating device according to another embodiment.

The aerosol generating device according to the embodiment of FIG. 6 includes a pressing member 70 that is provided in a path through which the protruding portion 51 moves and applies an elastic force (a resistive force) with respect to the movement of the protruding portion 51. An end 70a of the pressing member 70 is connected to the intermediate container 11, and the other end 70b of the pressing member 70 is connected to the protruding portion 51. The pressing member 70 may be a spring, and may apply an elastic force in a direction opposite to a direction in which the protruding portion 51 moves so that the rotating member 40 and the connector 50 rotate together and then the rotating member 40 and the connector 50 return to their original positions.

The embodiment is not limited by a configuration of the pressing member 70, and, for example, an elastic pressing member may include a compression cylinder using a liquid or a gas.

Figure 7:
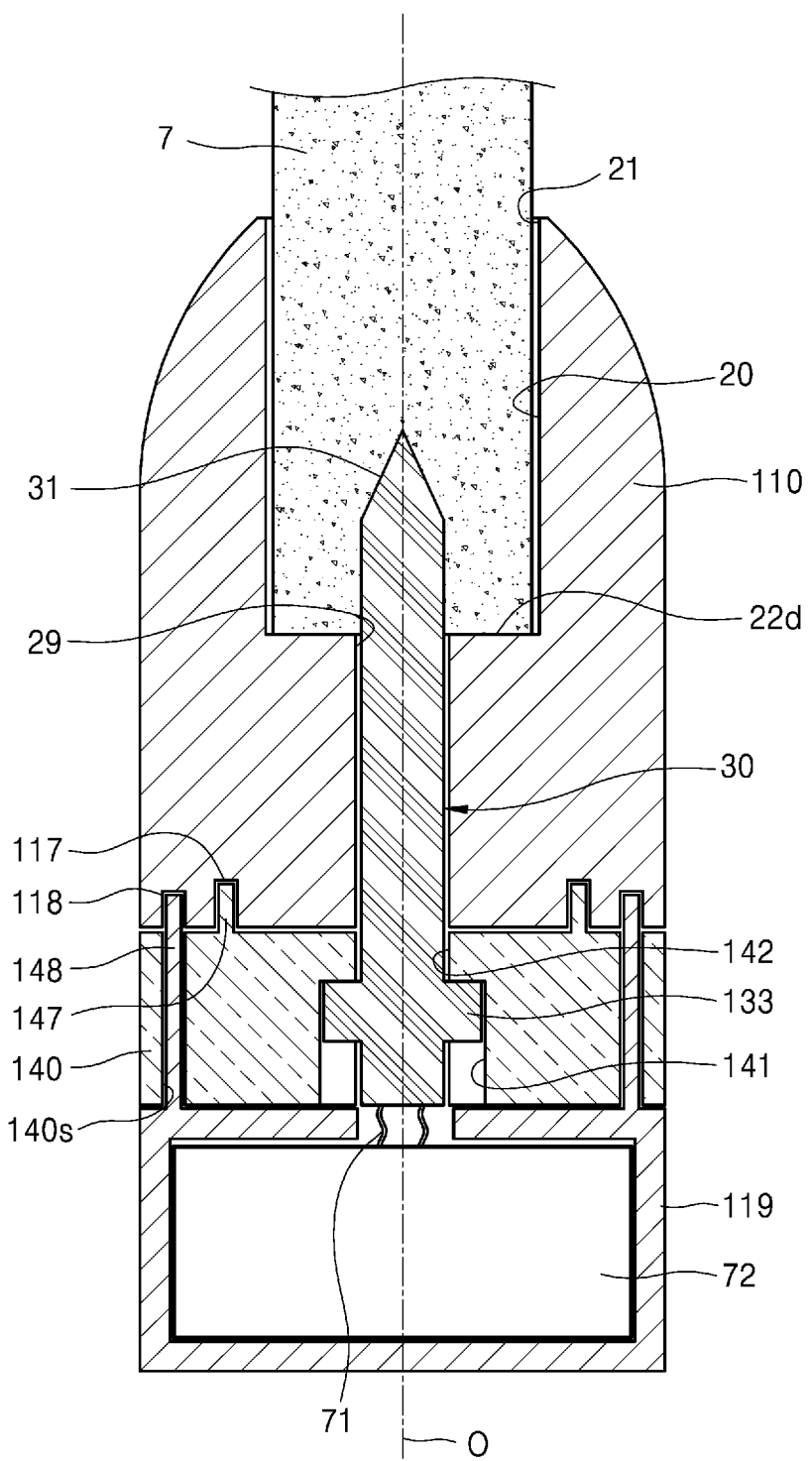
FIG. 7 is a longitudinal-sectional view of an aerosol generating device according to another embodiment.
Figure 8:
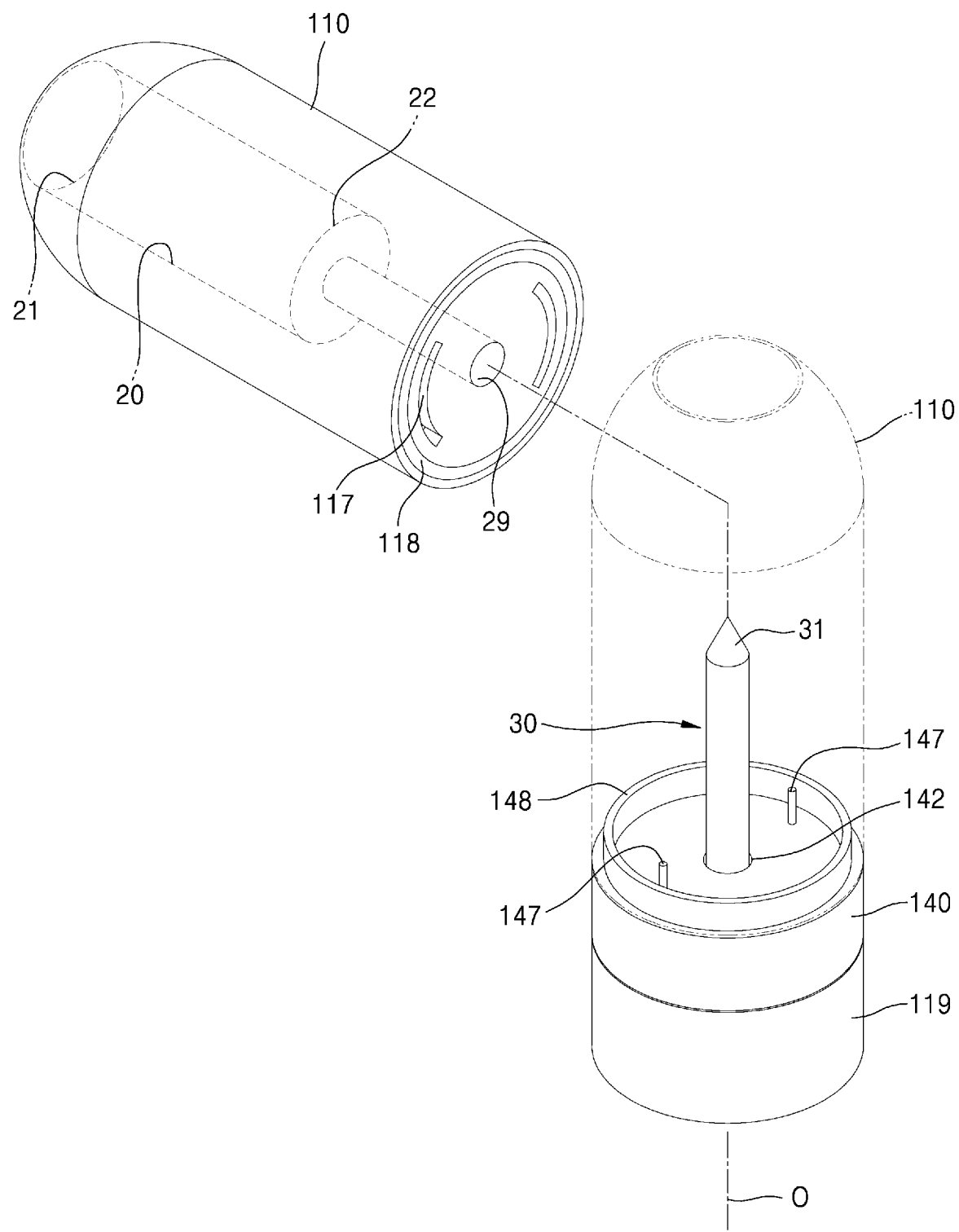
FIG. 8 is a perspective view illustrating a coupling relationship between elements of the aerosol generating device of FIG. 7.

FIG. 7 is a longitudinal-sectional view of an aerosol generating device according to another embodiment, and FIG. 8 is a perspective view illustrating a coupling relationship between elements of the aerosol generating device according to the embodiment of FIG. 7.

The aerosol generating device provided with a rotary heater according to the embodiment of FIGS. 7 and 8 includes a casing 110 having a hollow shape and including the path 20 in which the cigarette 7 is accommodated, a rotating member 140 rotatably coupled to the casing 110, and the heater 30 rotating along with the rotating member 140 and heating the cigarette 7.

The casing 110 may have a hollow cylindrical shape, and the casing 110 includes the path 20 having an inner diameter corresponding to an outer diameter of the cigarette 7 and accommodating the cigarette 7. The path 20 has the first opening 21 open at an end of the path 20 to the outside and a bottom portion 22d supporting a lower end portion of the cigarette 7 accommodated in the path 20.

The casing 110 has the hole 29 connected to the path 20 so that the first end portion 31 of the heater 30 passes through the hole 29. The hole 29 is formed to pass through a central area of the bottom portion 22d of the path 20.

The heater 30 that heats the cigarette 7 is provided in the casing 110. The first end portion 31 of the heater 30 is located inside the path 20 through the hole 29, and, when the cigarette 7 is accommodated in the casing 10, the first end portion 31 of the heater 30 is inserted into an end portion of the cigarette 7.

The second end portion 32 of the heater 30 is electrically connected to the electricity supplying device 72 located at a rear portion of the casing 110 through the electrical wiring 71. A base 119 surrounding the electricity supplying device 72 is connected to the rear portion of the casing 110. The base 119 may rotatably support the rotating member 140 so that the rotating member 140 may rotate along with the casing 110.

When electricity of the electricity supplying device 72 is supplied to the heater 30 in a state where the cigarette 7 is inserted into the first end portion 31 of the heater 30, the cigarette 7 is heated.

The rotating member 140 is rotatably coupled to the casing 110 to rotate about the central axis O in a longitudinal direction of the path 20. When the user holds the rotating member 140 in his/her hand and rotates the rotating member 140, the rotating member 140 rotates about the central axis O, and the heater 30 also rotates about the central axis O along with the rotating member 140.

The rotating member 140 is rotatably coupled to the casing 110. The rotating member 140 has a hollow cylindrical shape whose inside is empty.

The rotating member 140 has a through-hole 142 through which the first end portion 31 of the heater 30 passes. Also, the rotating member 140 includes a groove portion 141 formed in an inner surface of the rotating member 140. The heater 30 includes a protruding portion 133 having a shape corresponding to the groove portion 141 of the rotating member 140 and protruding outward from an outer surface of the heater 30.

When the first end portion 31 of the heater 30 passes through the through-hole 142 of the rotating member 140, the protruding portion 133 protruding from the outer surface of the heater 30 is inserted into the groove portion 141 of the rotating member 140, and thus the heater 30 is coupled to the rotating member 140 and the rotating member 140 and the heater 30 form one body rotating together.

Although only a configuration in which the protruding portion 133 is formed on the heater 30 and the groove portion 141 is formed in the rotating member 140 is described in the embodiment, the embodiment is not limited by the configuration, and, for example, a groove portion may be formed in the heater 30 and a protruding portion may be formed on the rotating member 140.

A movement protrusion 147 is formed on a surface of the rotating member 140 facing the casing 110. A guide groove portion 117 into which the movement protrusion 147 may be inserted is formed in a surface of the casing 110 facing the rotating member 140. The guide groove portion 117 is formed to extend by a pre-determined distance in a circumferential direction about the center of rotation of the rotating member 140.

The base 119 includes a flange 148 protruding toward the rotating member 140. The flange 148 extends in the circumferential direction about the central axis O that is the center of rotation of the rotating member 140. The flange 148 protrudes from the base 119 coupled to the rear portion of the casing 110 and passes through a connection path 140s extending in the circumferential direction of the rotating member 140 to be coupled to a flange groove 118 of the casing 110. Accordingly, the rotating member 140 is rotatably supported about the central axis O by the flange 148 between the casing 110 and the base 119.

While the rotating member 140 rotates relative to the casing 110, the movement protrusion 147 of the rotating member 140 moves along the guide groove portion 117 in a state where the movement protrusion 147 is inserted into the guide groove portion 117 of the casing 110. When the movement protrusion 147 reaches an end portion of the guide groove portion 117, the end portion of the guide groove portion 117 limits further movement of the movement protrusion 147, thereby limiting the rotation of the rotating member 140.

As the rotating member 140 rotates, the heater 30 connected to the rotating member 140 rotates along with the rotating member 140. Because the movement protrusion 147 of the rotating member 140 may rotate along the guide groove portion 117 of the casing 110, the rotating member 140 and the heater 30 may rotate together within a range where the movement protrusion 147 may move along the guide groove portion 117.

When a user rotates the rotating member 140 before the cigarette 7 is removed from the aerosol generating device according to the embodiment of FIGS. 7 and 8, the heater 30 rotates about the central axis O along with the rotating member 140. While the heater 30 rotates, a position of the cigarette 7 with respect to the casing 110 is not changed and is maintained.

When the heater 30 rotates in a state where the first end portion 31 of the heater 30 is inserted into the cigarette 7, contact surfaces between the cigarette 7 and the heater 30 which are attached to each other due to a tobacco material trapped in the contact surfaces between the cigarette 7 and the heater 30 may be easily separated from each other.

When the heater 30 rotates and thus the contact surfaces between the heater 30 and the cigarette 7 are separated from each other, the user may hold the cigarette 7 and pull the cigarette 7 out of the path 20 of the casing 110, to completely separate the cigarette 7 from the casing 110 of the aerosol generating device.

Because the heater 30 is first separated from the cigarette 7 through the above operation, and then the user may hold the cigarette 7 and may separate the cigarette 7 from the aerosol generating device, a residue transferred to the cigarette 7 may be easily discharged to the outside of the aerosol generating device along with the cigarette 7.

Embodiments of FIGS. 9 through 21F illustrate a modified aerosol generating device and a modified aerosol generating method applicable to the aerosol generating device according to any of the embodiments of FIGS. 1 through 8.

Reference numerals denoting elements in FIGS. 9 through 21F are independently used without being associated with reference numerals used in FIGS. 1 through 8. Accordingly, it should be understood that reference numerals denoting elements in FIGS. 1 through 8 and reference numerals denoting elements in FIGS. 9 through 21F are used to denote different elements independent from each other.

Figure 9:
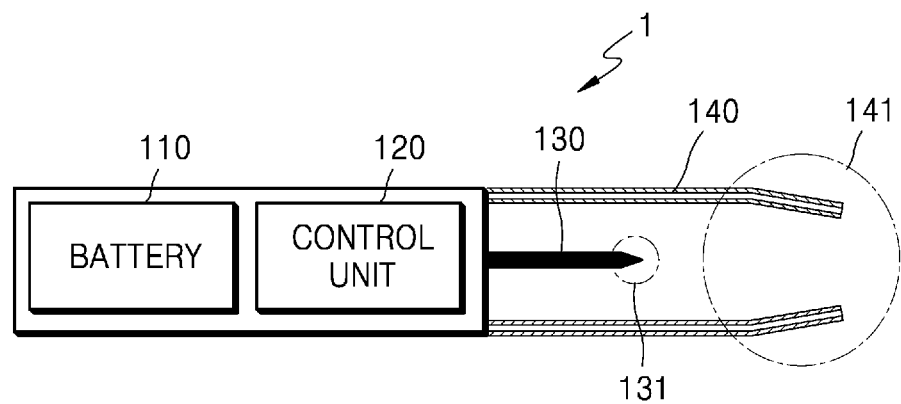
FIG. 9 is a block diagram showing an example of an aerosol generating apparatus according to another embodiment.

FIG. 9 is a block diagram showing an example of an aerosol generating apparatus according to another embodiment.

Referring to FIG. 9, aerosol generating device 1, hereinafter, referred to as "holder", includes battery 110, control unit 120, and heater 130. The holder 1 also includes an internal space formed by the casing 140. A cigarette may be inserted into the internal space of the holder 1.

FIG. 9 shows holder 1 with some elements related to the embodiment. Therefore, It will be understood by one of ordinary skill in the art that the holder 1 may further include additional conventional elements.

When a cigarette is inserted into the holder 1, the holder 1 heats the heater 130. The temperature of an aerosol generating material in the cigarette is raised by the heated heater 130, and thus aerosol is generated. The generated aerosol is delivered to a user through a cigarette filter. However, even when a cigarette is not inserted into the holder 1, the holder 1 may heat the heater 130.

The casing 140 may be detached from the holder 1. For example, when a user rotates the casing 140 clockwise or counterclockwise, the casing 140 may be detached from the holder 1.

The diameter of a hole formed by a terminal end 141 of the casing 140 may be smaller than the diameter of a space formed by the casing 140 and the heater 130. In this case, the hole may serve as a guide for a cigarette inserted into the holder 1.

The battery 110 supplies power used for the holder 1 to operate. For example, the battery 110 may supply power for heating the heater 130 and supply power for operating the control unit 120. In addition, the battery 110 may supply power for operating a display, a sensor, a motor, and the like installed in the holder 1.

The battery 110 may be a lithium iron phosphate ($LiFePO_4$) battery, but is not limited to the example described above. For example, the battery 110 may be a lithium cobalt oxide ($LiCoO_2$) battery, a lithium titanate battery, etc.

Also, the battery 110 may have a cylindrical shape having a diameter of 10 mm and a length of 37 mm, but is not limited thereto. The capacity of the battery 110 may be 120 mAh or more, and the battery 110 may be a rechargeable battery or a disposable battery. For example, when the battery 110 is rechargeable, the charging rate (C-rate) of the battery 110 may be 10C and the discharging rate (C-rate) may be 16C to 20C. However, the present disclosure is not limited thereto. Also, for stable use, the battery 110 may be manufactured, such that 80% or more of the total capacity may be ensured even when charging/discharging are performed 8000 times.

Here, it may be determined whether the battery 110 is fully charged or completely discharged based on a level of power stored in the battery 110 as compared to the entire capacity of the battery 110. For example, when power stored in the battery 110 is equal to or more than 95% of the total capacity, it may be determined that the battery 110 is fully charged. Furthermore, when power stored in the battery 110 is 10% or less of the total capacity, it may be determined that the battery 110 is completely discharged. However, the criteria for determining whether the battery 110 is fully charged or completely discharged are not limited to the above examples.

The heater 130 is heated by power supplied from the battery 110. When a cigarette is inserted into the holder 1, the heater 130 is located inside the cigarette. Therefore, the heated heater 130 may raise the temperature of an aerosol generating material in the cigarette.

The shape of the heater 130 may be a combination of a cylindrical shape and a conical shape. For example, heater 130 may have a diameter of 2 mm, a length of 23 mm, and a cylindrical shape. Also, end 131 of heater 130 may be processed to have an acute angle edge. But, the embodiments are not limited to these features. In other words, the heater 130 may have any shape as long as the heater 130 may be inserted into the cigarette. In addition, only a portion of the heater 130 may be heated. For example, if the heater 130 has a length of 23 mm, only a part of the heater 130, 12 mm distanced from the end 131, is heated, while other part of the heater 130 is not heated.

The heater 130 may be an electrical resistive heater. For example, the heater 130 includes an electrically conductive track, and the heater 130 may be heated as current flows through the electrically conductive track.

For stable use, the heater 130 may be supplied with power according to the specifications of 3.2 V, 2.4 A, and 8 W, but is not limited thereto. For example, when power is supplied to the heater 130, the surface temperature of the heater 130 may rise to 400° C. or higher. The surface temperature of the heater 130 may rise to about 350° C. before 15 seconds after the power supply to the heater 130 starts.

The holder 1 may have a special temperature sensor. Alternatively, the holder 1 may not be provided with a temperature sensing sensor, and the heater 130 may serve as a temperature sensing sensor. For example, the heater 130 may further include a second electrically conductive track for sensing temperature in addition to a first electrically conductive track for sensing heating temperature.

For example, when a voltage applied to the second electrically conductive track and a current flowing through the second electrically conductive track are measured, a resistance R may be determined. At this time, a temperature T of the second electrically conductive track may be determined by Equation 1 below.

$$R=R_0\{1+\alpha(T-T_0)\} \quad [\text{Equation 1}]$$

In Equation 1, R denotes a current resistance value of the second electrically conductive track, $R_0$ denotes a resistance value at a temperature $T_0$ (e.g., 0° C.), and a denotes a resistance temperature coefficient of the second electrically conductive track. Since conductive materials (e.g., metals) have inherent resistance temperature coefficients, a may be determined in advance according to a conductive material constituting the second electrically conductive track. Therefore, when the resistance R of the second electrically conductive track is determined, the temperature T of the second electrically conductive track may be calculated according to Equation 1.

The heater 130 may include at least one electrically conductive track (a first electrically conductive track and a second electrically conductive track). For example, the heater 130 may include, but is not limited to, two first electrically conductive tracks and one or two second electrically conductive tracks.

An electrically conductive track includes an electro-resistive material. For example, an electrically conductive track may include a metal. In another example, an electrically conductive track may include an electrically conductive ceramic material, a carbon, a metal alloy, or a composite of a ceramic material and a metal.

In addition, the holder 1 may include both an electrically conductive track, which serves as temperature sensing sensors, and a temperature sensing sensor.

The control unit 120 controls the overall operation of the holder 1. Specifically, the control unit 120 controls not only operations of the battery 110 and the heater 130, but also operations of other components included in the holder 1. The control unit 120 may also check the status of each of the components of the holder 1 and determine whether the holder 1 is in an operable state.

The control unit 120 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

For example, the control unit 120 may control the operation of the heater 130. The control unit 120 may control an amount of power supplied to the heater 130 and a time for supplying the power, such that the heater 130 may be heated to a predetermined temperature or maintained at a proper temperature. The control unit 120 may also check the status of the battery 110 (e.g., the remaining amount of the battery 110) and generate a notification signal as occasions demand.

Also, the control unit 120 may check the presence or absence of a user's puff, check the strength of the puff, and count the number of puffs. Also, the control unit 120 may continuously check the time during which the holder 1 is operating. The control unit 120 may also check whether a cradle 2 to be described below is coupled with the holder 1 and control the operation of the holder 1 based on whether the cradle 2 is coupled with or separated from and the holder 1.

Meanwhile, the holder 1 may further include general-purpose components other than the battery 110, the control unit 120, and the heater 130.

For example, the holder 1 may include a display capable of outputting visual information or a motor for outputting tactile information. For example, when a display is included in the holder 1, the control unit 120 may provide a user information about the state of the holder 1 (e.g., availability of the holder, etc.), information about the heater 130 (e.g., start of preheating, progress of preheating, completion of preheating, etc.), information about the battery 110 (e.g., remaining power of the battery 110, availability, etc.), information about resetting of the holder 1 (e.g., reset timing, reset progress, reset completion, etc.), information about cleaning of the holder 1 (e.g., cleaning timing, cleaning progress, cleaning completion, etc.), information about charging of the holder 1 (e.g., need of charging, charging progress, charging completed, etc.), information about puff (e.g., the number of puffs, notification of expected completion of puffs, etc.), or information about safety (e.g., time of use, etc.) via the display. In another example, when a motor is included in the holder 1, the control unit 120 may transmit the above-described information to a user by generating a vibration signal by using the motor.

The holder 1 may also include a terminal coupled with at least one input device (e.g., a button) and/or the cradle 2 through which a user may control the function of the holder 1. For example, a user may perform various functions by using the input device of the holder 1. By adjusting the number of times a user presses the input device (e.g., once, twice, etc.) or the time during which the input device is being pressed (e.g., 0.1 second, 0.2 second, etc.), a desired function from among a plurality of functions of the holder 1 may be executed. As a user manipulates the input device, the holder 1 may perform a function of preheating the heater 130, a function of regulating the temperature of the heater 130, a function of cleaning the space in which a cigarette is inserted, a function of checking whether the battery 110 is in an operable state, a function of displaying the remaining power (available power) of the battery 110, a function of resetting the holder 1, etc. However, the functions of the holder 1 are not limited to the examples described above.

The holder 1 may also include a puff detecting sensor, a temperature sensing sensor, and/or a cigarette insertion detecting sensor. For example, the puff detecting sensor may be implemented by a conventional pressure sensor, and cigarette insertion detecting sensor may be implemented by a general capacitance sensor or electric resistive sensor. Also, the holder 1 may be fabricated to have a structure in which the outside air may flow in/out even in the state where the cigarette is inserted.

Figure 10A:
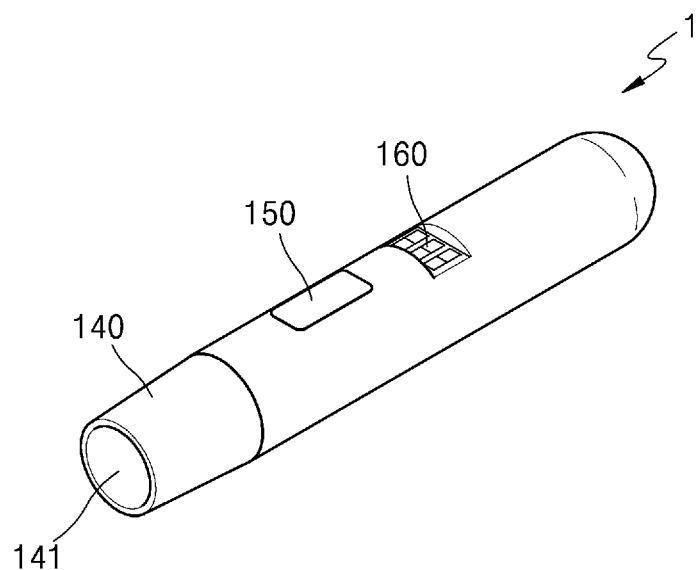
FIGS. 10A and 10B are diagrams showing various views of an example of a holder.
Figure 10B:
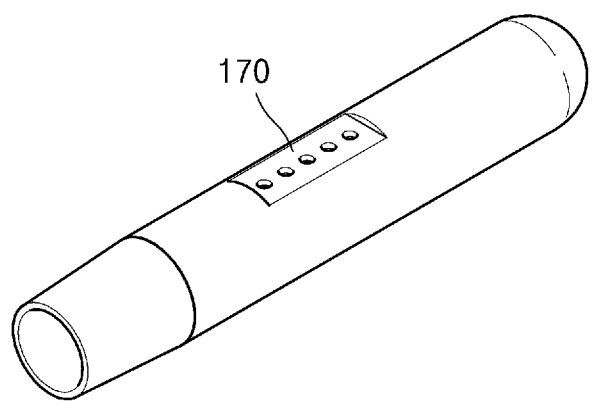

FIGS. 10A and 10B are diagrams showing various views of an example of a holder.

FIG. 10A is a diagram showing an example of holder 1 seen from a first direction. As shown in FIG. 10A, holder 1 may be fabricated to have a cylindrical shape, but not limited thereto. The casing 140 of the holder 1 may be separated by an action of a user and a cigarette may be inserted into a terminal end 141 of the casing 140. The holder 1 may also include a button 150 for a user to control the holder 1 and a display 160 for outputting an image.

FIG. 10B is a diagram showing other example of holder 1 seen from a second direction. The holder 1 may include a terminal 170 coupled with the cradle 2. As the terminal 170 of the holder 1 is coupled with a terminal 260 of the cradle 2, the battery 110 of the holder 1 may be charged by power supplied by a battery 210 of the cradle 2. Also, the holder 1 may be operated by power supplied from the battery 210 of the cradle 2 through the terminal 170 and the terminal 260 and a communication (transmission/reception of signals) may be performed between the holder 1 and the cradle 2 through the terminal 170 and the terminal 260. For example, the terminal 170 may include four micro pins, but the present disclosure is not limited thereto.

Figure 11:
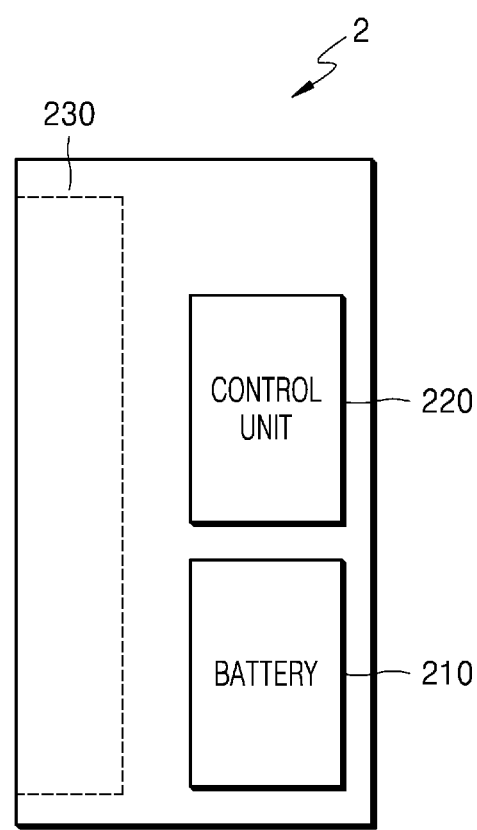
FIG. 11 is a diagram showing an example configuration of a cradle.

FIG. 11 is a diagram showing an example configuration of a cradle.

In FIG. 11, the cradle 2 includes a battery 210 and a control unit 220. The cradle 2 also includes an internal space 230 into which the holder 1 may be inserted. For example, the internal space 230 may be formed on one side of the cradle 2. Therefore, the holder 1 may be inserted and fixed in the cradle 2 even when the cradle 2 does not include a separate lid.

FIG. 11 shows the cradle 2 having some elements related to the embodiments. Therefore, It will be understood by one of ordinary skill in the art that the cradle 2 may further include additional conventional elements in addition to the elements shown in FIG. 11.

The battery 210 provides power used to operate the cradle 2. In addition, the battery 210 may supply power for charging the battery 110 of the holder 1. For example, when the holder 1 is inserted into the cradle 2 and the terminal 170 of the holder 1 is coupled with the terminal 260 of the cradle 2, the battery 210 of the cradle 2 may supply power to the battery 110 of the holder 1.

Also, when the holder 1 is coupled with the cradle 2, the battery 210 may supply power used for the holder 1 to operate. For example, when the terminal 170 of the holder 1 is coupled with the terminal 260 of the cradle 2, the holder 1 may operate by using power supplied by the battery 210 of the cradle 2 regardless of whether the battery 110 of the holder 1 is discharged or not.

The examples of type of battery 210 may be the same as the battery 110 shown in FIG. 9. The battery 210 may have capacity bigger than the capacity of battery 110. For example, the battery may have capacity over 3000 mAh. But, the capacity of the battery 210 should not be limited to the above example.

The control unit 220 generally controls the overall operation of the cradle 2. The control unit 220 may control the overall operation of all the configurations of the cradle 2. The control unit 220 may also determine whether the holder 1 is coupled with the cradle 2 and control the operation of the cradle 2 according to coupling or separation of the cradle 2 and the holder 1.

For example, when the holder 1 is coupled with the cradle 2, the control unit 220 may supply power of the battery 210 to the holder 1, thereby charging the battery 110 or heating the heater 130. Therefore, even when remaining power of the battery 110 is low, a user may continuously smoke by coupling the holder 1 with the cradle 2.

The control unit 120 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

Meanwhile, the cradle 2 may further include general-purpose components other than the battery 210 and the control unit 220. For example, cradle 2 may include a display capable of outputting visual information. For example, when the cradle 2 includes a display, the control unit 220 generates a signal to be displayed on the display, thereby informing a user information regarding the battery 210 (e.g., the remaining power of the battery 210, availability of the battery 210, etc.), information regarding resetting of the cradle 2 (e.g., reset timing, reset progress, reset completion, etc.), information regarding cleaning of the holder 1 (e.g., cleaning timing, cleaning necessity, cleaning progress, cleaning completion, etc.), information regarding charging of the cradle 2 (e.g., charging necessity, charging progress, charging completion, etc.).

The cradle 2 may also include at least one input device (e.g., a button) for a user to control the function of the cradle 2, a terminal 260 to be coupled with the holder 1, and/or an interface for charging the battery 210 (e.g., an USB port, etc.).

For example, a user may perform various functions by using the input device of the cradle 2. By controlling the number of times that a user presses the input device or a period of time for which the input device is pressed, a desired function from among the plurality of functions of the cradle 2 may be executed. As a user manipulates the input device, the cradle 2 may perform a function of preheating the heater 130, a function of regulating the temperature of the heater 130, a function of cleaning the space in which a cigarette is inserted, a function of checking whether the cradle 2 is in an operable state, a function of displaying the remaining power (available power) of the battery 210 of the cradle 2, a function of resetting the cradle 2, etc. However, the functions of the cradle 2 are not limited to the examples described above.

Figure 12A:
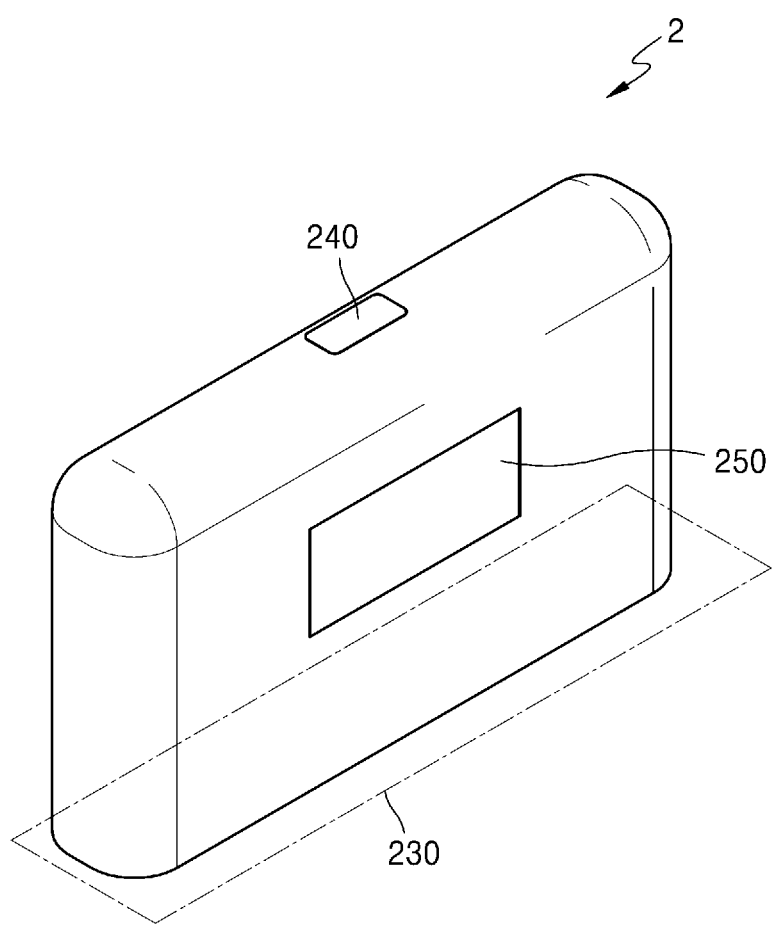
FIGS. 12A and 12B are diagrams showing various views of an example of a cradle.
Figure 12B:
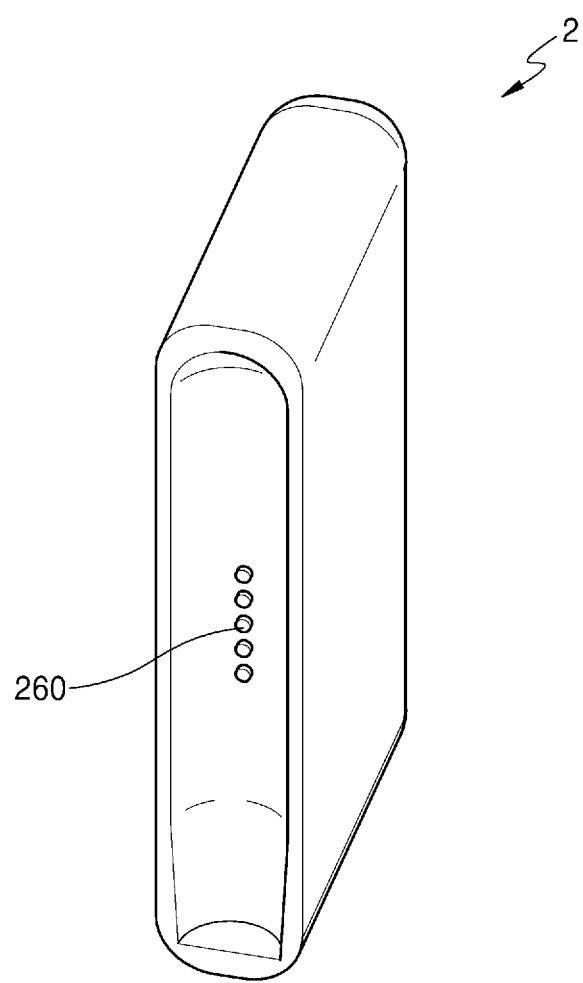

FIGS. 12A and 12B are diagrams showing various views of an example of a cradle.

FIG. 12A is a diagram showing an example of the cradle 2 seen from a first direction. The internal space 230 into which the holder 1 may be inserted may be formed on one side of the cradle 2. Also, the holder 1 may be inserted and fixed in the cradle 2 even when the cradle 2 does not include a separate fixing unit like a lid. The cradle 2 may also include a button 240 for a user to control the cradle 2 and a display 250 for outputting an image.

FIG. 12B is a diagram showing other example of the cradle 2 seen from a second direction. The cradle 2 may include a terminal 260 to be coupled with the inserted holder 1. The battery 110 of the holder 1 may be charged by power supplied by the battery 210 of the cradle 2 as the terminal 260 is coupled with the terminal 170 of the holder 1. Also, the holder 1 may be operated by power supplied from the battery 210 of the cradle 2 through the terminal 170 and the terminal 260 and transmission/reception of signals may be performed between the holder 1 and the cradle 2 through the terminal 170 and the terminal 260. For example, the terminal 260 may include four micro pins, but the present disclosure is not limited thereto.

As above explained along with FIGS. 12A and 12B, holder 1 may be inserted into internal space 230. The holder 1 may be completely inserted into the cradle 2 or may be tilted while being inserted into the cradle 2. Hereinafter, referring to FIGS. 13 to 15B, examples of inserting holder 1 into cradle 2 will be explained.

Figure 13:
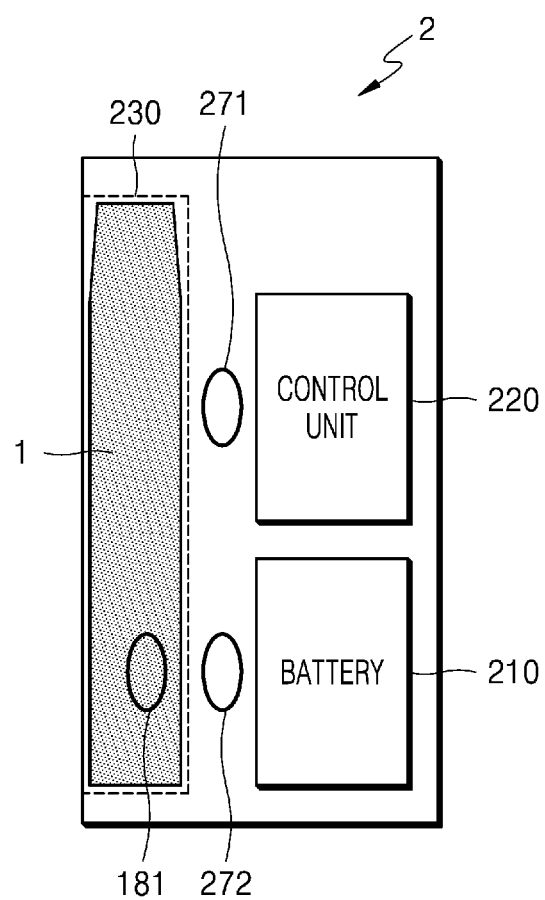
FIG. 13 is a diagram showing an example in which a holder is inserted into a cradle.

FIG. 13 is a diagram showing an example in which a holder is inserted into a cradle.

FIG. 13 shows an example where the holder 1 is inserted into the cradle 2. Since the space 230 into which the holder 1 is to be inserted is present on one side surface of the cradle 2, the inserted holder 1 may not be exposed to the outside by the other side surfaces of the cradle 2. Therefore, the cradle 2 may not include another component (e.g., a lid) for not exposing the holder 1 to the outside.

The cradle 2 may include at least one attaching member 271 and/or 272 to increase attachment strength with the holder 1. Also, at least one attaching member 181 may be included in the holder 1 as well. Here, attaching members 181, 271, and 272 may be magnets, but are not limited thereto. In FIG. 13, for a purpose of a simple explanation, it is shown that the holder 1 includes only one attaching member 181 and the cradle 2 includes two the attaching members 271 and 272. But, the number of the attaching members 181, 271 and 272 are not limited.

The holder 1 may include the attaching member 181 at a first position and the cradle 2 may include the attaching members 271 and 272 at a second position and a third position, respectively. In this case, the first position and the third position may be positions facing each other when the holder 1 is inserted into the cradle 2.

Since the attaching members 181, 271, and 272 are included in the holder 1 and the cradle 2, the holder 1 and the cradle 2 may be attached to each other more strongly even when the holder 1 is inserted into one side surface of the cradle 2. In other words, as the holder 1 and the cradle 2 further include the attaching members 181, 271, and 272 in addition to the terminals 170 and 260, the holder 1 and the cradle 2 may be attached to each other more strongly. Therefore, even when there is no separate component (e.g., a lid) in the cradle 2, the inserted holder 1 may not be easily separated from the cradle 2.

Also, if it is determined that the holder 2 is fully inserted into the cradle 2 through the terminals 170, 260 and/or the attaching members 271 and 272, the control unit 220 may charge the battery 110 of the holder 1 using electrical power of the battery 210.

Figure 14:
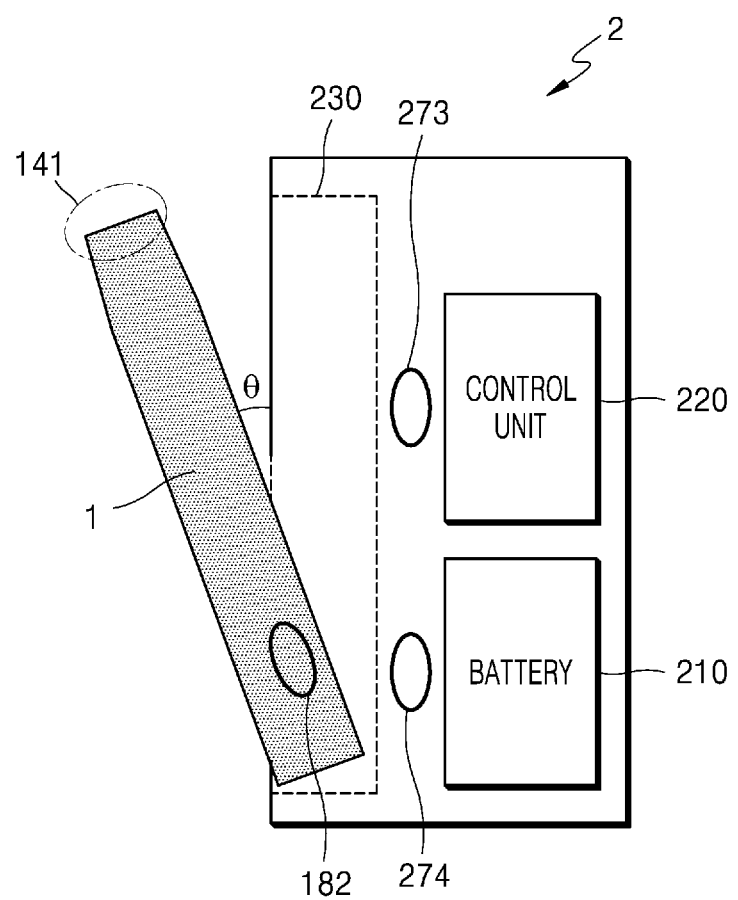
FIG. 14 is a diagram showing an example in which a holder is tilted while being inserted into a cradle.

FIG. 14 is a diagram showing an example in which a holder is tilted while being inserted into a cradle.

FIG. 14 shows that the holder 1 is tilted inside the cradle 2. Here, the term 'tilting' indicates that the holder 1 is inclined at a certain angle in a state while the holder 1 is being inserted into the cradle 2.

If the holder 1 is fully tilted inside the cradle 2 as shown in FIG. 13, the user may not smoke. In other words, once the holder 1 is completely inserted into the cradle 2, a cigarette may not be inserted into the holder 1. Therefore, when the holder 1 is completely inserted into the cradle 2, a user may not smoke.

If the holder 1 is tilted as shown in FIG. 14, end 141 of the holder 1 is exposed to outside. Therefore, the user may insert a cigarette into the terminal end 141 and smoke generated aerosol. When a cigarette is inserted into the end 141 of the holder, tilting angle θ may setup to secure an enough angle in which the cigarette may not be bent or damaged. For example, the holder 1 may be tilted so that a whole part of cigarette insertion opening included in the end 141 may be exposed to the outside. For example, tilting angle θ may range between 0 to 180 degrees, preferably between 10 degrees and 90 degrees. More preferably, tilting angle θ may range between 10 to 20 degrees, between 10 to 30 degrees, between 10 to 40 degrees, between 10 to 50 degrees, or between 10 to 60 degrees.

Also, even in the state that the holder 1 is tilted, the terminal 170 of the holder and the terminal 260 of the cradle 2 are coupled to each other. Therefore, the heater 130 of the holder 1 may be heated by power supplied by the battery 210 of the cradle 2. Therefore, the holder 1 may generate aerosol by using the battery 210 of the cradle 2 even when the remaining power of the battery 110 of the holder 1 is low or the battery 110 of the holder 1 is completely discharged.

FIG. 14 shows an example where the holder includes one attaching member 182 and the cradle 2 includes two attaching member 273, 274. For example, each position of the attaching members 182, 273, 274 is as shown in FIG. 13. Assuming that the attaching members 182, 273, and 274 are magnets, the magnetic strength of the attaching member 274 may be greater than the magnetic strength of the attaching member 273. Therefore, the holder 1 may not be completely separated from the cradle 2 due to the attaching member 182 and the attaching member 274 even when the holder 1 is tilted.

Also, when it is determined that the holder 1 titled through the terminals 170 and 260 and/or the attaching members 181, 271, and 272, the control unit 220 may heat the heater 130 of the holder 1 or charge the battery 110 by using power of the battery 210.

Figure 15A:
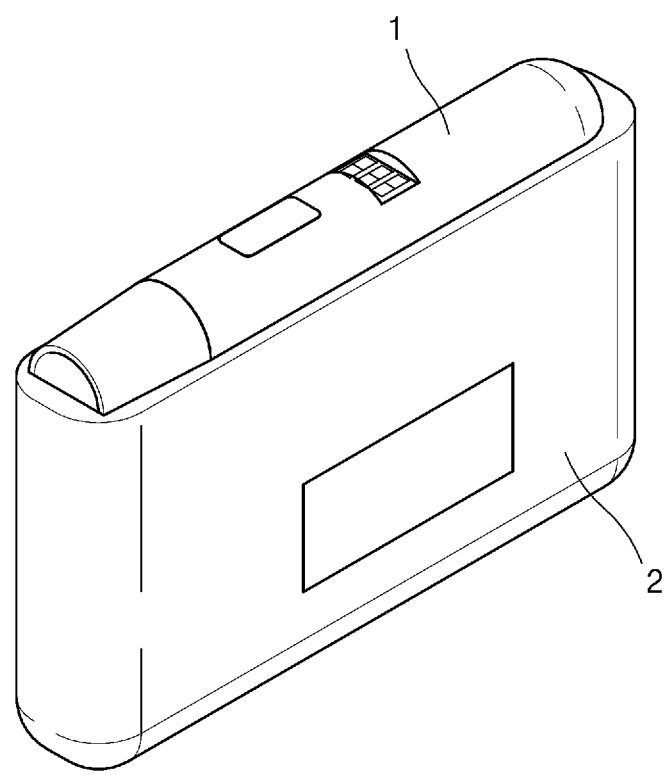
FIGS. 15A to 15B are diagrams showing examples in which a holder is inserted into a cradle.
Figure 15B:
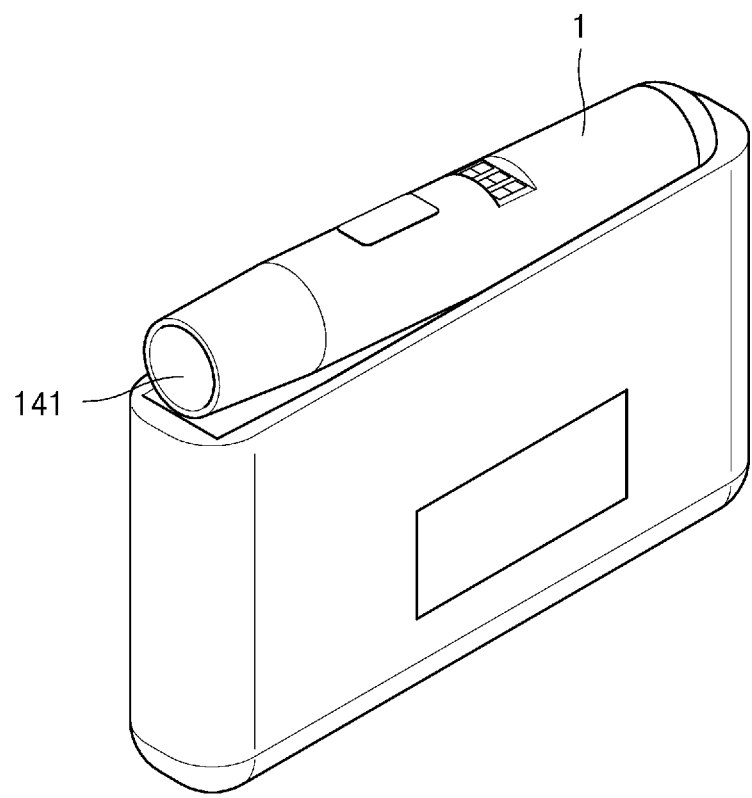

FIGS. 15A to 15B are diagrams showing examples in which a holder is inserted into a cradle.

FIG. 15A shows an example where the holder 1 is fully inserted into the cradle 2. The cradle 2 may be fabricated to provide the sufficient internal space 230 of the cradle 2 to minimize the contact of a user with the holder 1 when the holder 1 is completely inserted into the cradle 2. When the holder 1 is completely inserted into the cradle 2, the control unit 220 supplies power of the battery 210 to the holder 1, such that the battery 110 of the holder 1 is charged.

FIG. 15B shows other example where the holder 1 is tilted while in the state of being inserted into the cradle 2. When the holder 1 is tilted, the control unit 220 supplies power of the battery 210 to the holder 1, such that the battery 110 of the holder 1 is charged or the heater 130 of the holder 1 is heated.

Figure 16:
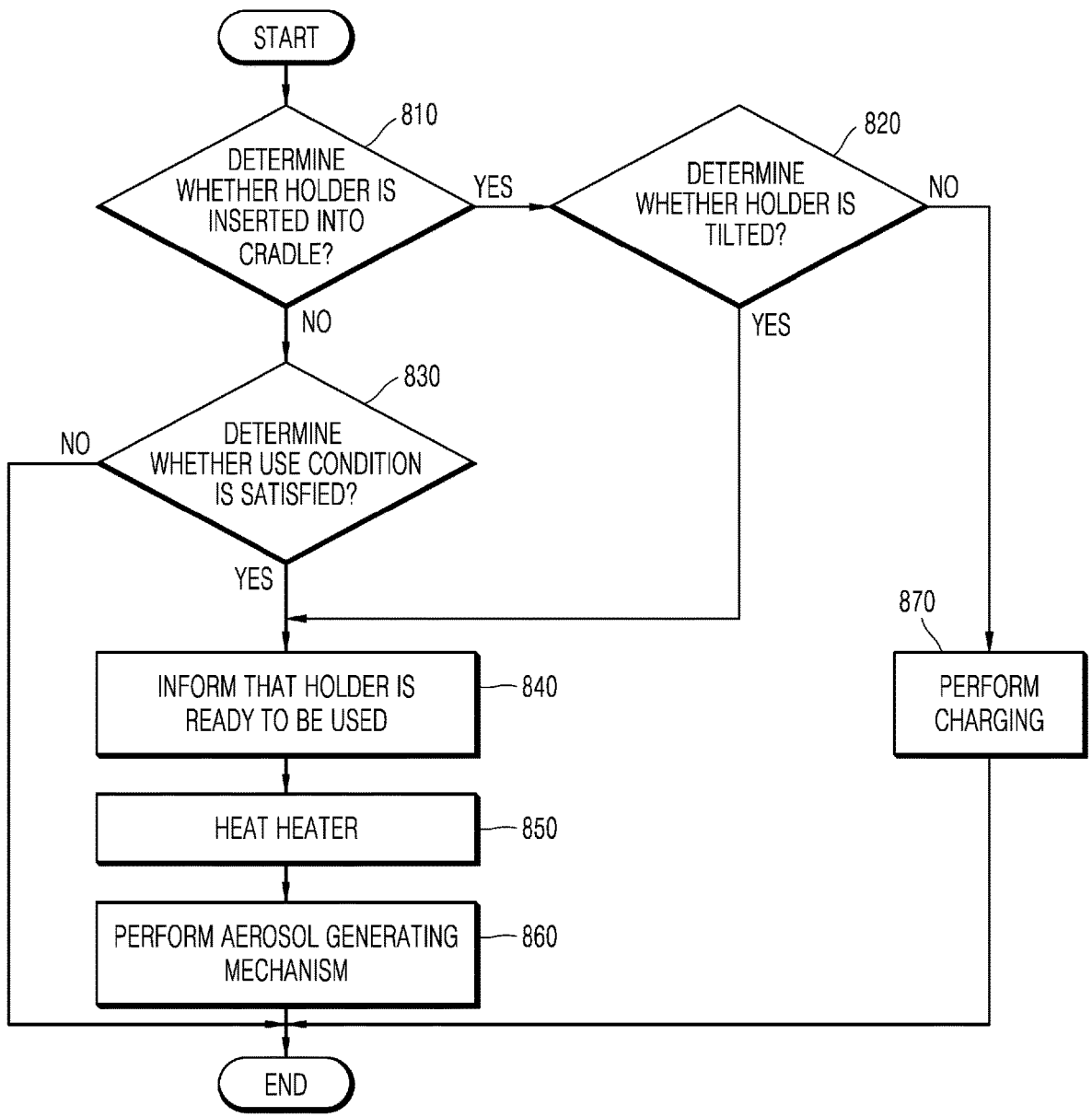
FIG. 16 is a flowchart for describing an example in which a holder and a cradle operate.

FIG. 16 is a flowchart for describing an example in which a holder and a cradle operates.

A method for generating aerosols shown in FIG. 16 includes operations that are performed in a time-series manner by the holder 1 shown in FIG. 9 or the cradle 2 shown in FIG. 11. Therefore, it will be understood that the descriptions given above with respect to the holder 1 shown in FIG. 9 and the cradle 2 shown in FIG. 11 also apply to the method of FIG. 16, even when the descriptions are omitted below.

In operation 810, the holder 1 determines whether it is inserted in the cradle 2. For example, the control unit 120 may determine whether the holder 1 is inserted into the cradle 2 based on whether the terminals 170 and 260 of the holder 1 and the cradle 2 are connected to each other and/or whether the attaching members 181, 271, and 272 are operating.

When the holder 1 is inserted into the cradle 2, the method proceeds to operation 820. When the holder 1 is separated from the cradle 2, the method proceeds to operation 830.

In operation 820, the cradle 2 determines whether the holder 1 is tilted. For example, the control unit 220 may determine whether the holder 1 is inserted into the cradle 2 based on whether the terminals 170 and 260 of the holder 1 and the cradle 2 are connected to each other and/or whether attaching members 182, 273, and 274 are operating.

Although it is described that the cradle 2 determines whether the holder 1 is tilted in operation 820, the present disclosure is not limited thereto. In other words, the control unit 120 of the holder 1 may determine whether the holder 1 is tilted.

When the holder 1 is tilted, the method proceeds to operation 840. When the holder 1 is not tilted (i.e., the holder 1 is completely inserted into the cradle 2), the method proceeds to operation 870.

In operation 830, the holder 1 determines whether conditions of using the holder 1 are satisfied. For example, the control unit 120 may determine whether the conditions for using the holder 1 are satisfied by checking whether the remaining power of the battery 110 and whether other components of the holder 1 may be normally operated.

When the conditions for using the holder 1 are satisfied, the method proceeds to operation 840. Otherwise, the method is terminated.

In operation 840, the holder 1 informs a user that the holder 1 is ready to be used. For example, the control unit 120 may output an image indicating that the holder 1 is ready to be used on the display of the holder 1 or may control the motor of the holder 1 to generate a vibration signal.

In operation 850, the heater 130 is heated. For example, when the holder 1 is separated from the cradle 2, the heater 130 may be heated by power of the battery 110 of the holder 1. In another example, when the holder 1 is tilted, the heater 130 may be heated by power of the battery 210 of the cradle 2.

The control unit 120 of the holder 1 or the control unit 220 of the cradle 2 may check the temperature of the heater 130 in real time and control an amount of power supplied to the heater 130 and a time for supplying the power to the heater 130. For example, the control unit 120 or 220 may check the temperature of the heater 130 in real time through a temperature sensor included in the holder 1 or an electrically conductive track of the heater 130.

In operation 860, the holder 1 performs an aerosol generation mechanism. For example, the control unit 120, 220 may check the temperature of the heater 130, which changes as a user performs puffs, and adjust an amount of power supplied to the heater 130 or stop supplying power to the heater 130. Also, the control unit 120 or 220 may count the number of puffs of the user and output information indicating that the holder 1 needs to be cleaned when the number of puffs reaches a certain number of times (e.g., 1500).

In operation 870, the cradle 2 performs charging of the holder 1. For example, the control unit 220 may charge the holder 1 by supplying power of the battery 210 of the cradle 2 to the battery 110 of the holder 1.

Meanwhile, the control unit 120 or 220 may stop the operation of the holder 1 according to the number of puffs of the user or the operation time of the holder 1. Hereinafter, an example in which the control unit 120 or 220 stops the operation of the holder 1 will be described with reference to FIG. 17.

Figure 17:
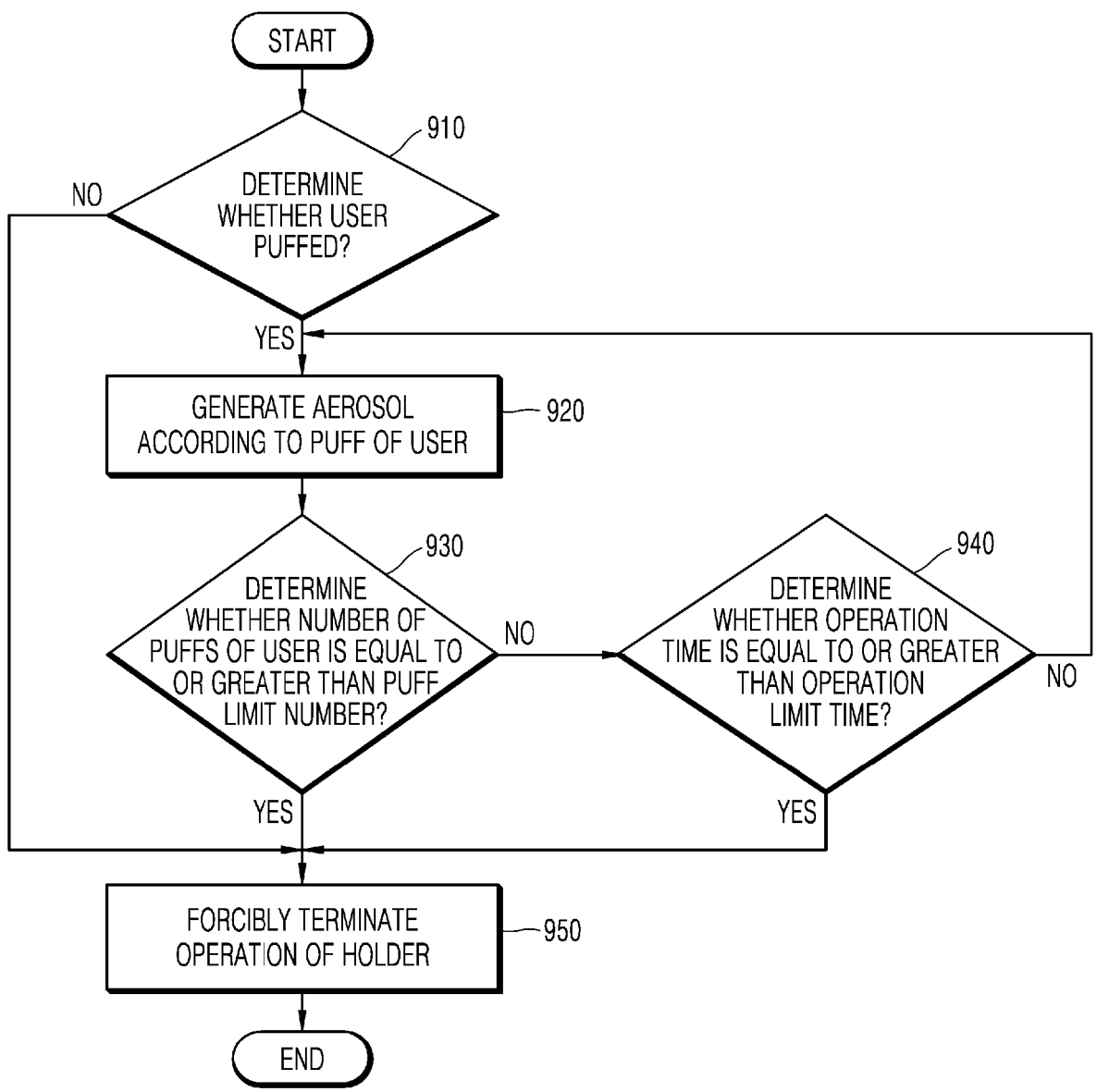
FIG. 17 is a flowchart for describing another example in which a holder operates.

FIG. 17 is a flowchart for describing another example in which a holder operates.

A method for generating aerosols shown in FIG. 17 includes operations that are performed in a time-series manner by the holder 1 shown in FIG. 9 and the cradle 2 shown in FIG. 11. Therefore, it will be understood that the descriptions given above with respect to the holder 1 shown in FIG. 9 or the cradle 2 shown in FIG. 11 also apply to the method of FIG. 17, even when the descriptions are omitted below.

In operation 910, the control unit 120 or 220 determines whether a user puffed. For example, the control unit 120 or 220 may determine whether the user puffed through the puff detecting sensor included in the holder 1.

In operation 920, aerosol is generated according to the puff of the user. The control unit 120 or 220 may adjust power supplied to the heater 130 according to the puff of the user and the temperature of the heater 130, as described above with reference to FIG. 16. Also, the control unit 120 or 220 counts the number of puffs of the user.

In operation 930, the control unit 120 or 220 determines whether the number of puffs of the user is equal to or greater than a puff limit number. For example, assuming that the puff limit number is set to 14, the control unit 120 or 220 determines whether the number of counted puffs is 14 or more.

On the other hand, when the number of puffs of the user is close to the puff limit number (e.g., when the number of puffs of the user is 12), the control unit 120 or 220 may output a warning signal through a display or a vibration motor.

When the number of puffs of the user is equal to or greater than the puff limit number, the method proceeds to operation 950. When the number of puffs of the user is less than the puff limit number, the method proceeds to operation 940.

In operation 940, the control unit 120 or 220 determines whether the operation time of the holder 1 is equal to or greater than an operation limit time. Here, the operation time of the holder 1 refers to accumulated time from a time point at which the holder 1 started its operation to a current time point. For example, assuming that the operation limit time is set to 10 minutes, the control unit 120 or 220 determines whether the holder 1 is operating for 10 minutes or longer.

On the other hand, when the operation time of the holder 1 is close to the operation limit time (e.g., when the holder 1 is operating for 8 minutes), the control unit 120 or 220 may output a warning signal through a display or a vibration motor.

When the holder 1 is operating for the operation limit time or longer, the method proceeds to operation 950. When the operation time of the holder 1 is less than the operation limit time, the method proceeds to operation 920.

In operation 950, the control unit 120 or 220 forcibly terminates the operation of the holder 1. In other words, the control unit 120 or 220 terminates the aerosol generation mechanism of the holder 1. For example, the control unit 120 or 220 may forcibly terminate the operation of the holder 1 by interrupting the power supplied to the heater 130.

Figure 18:
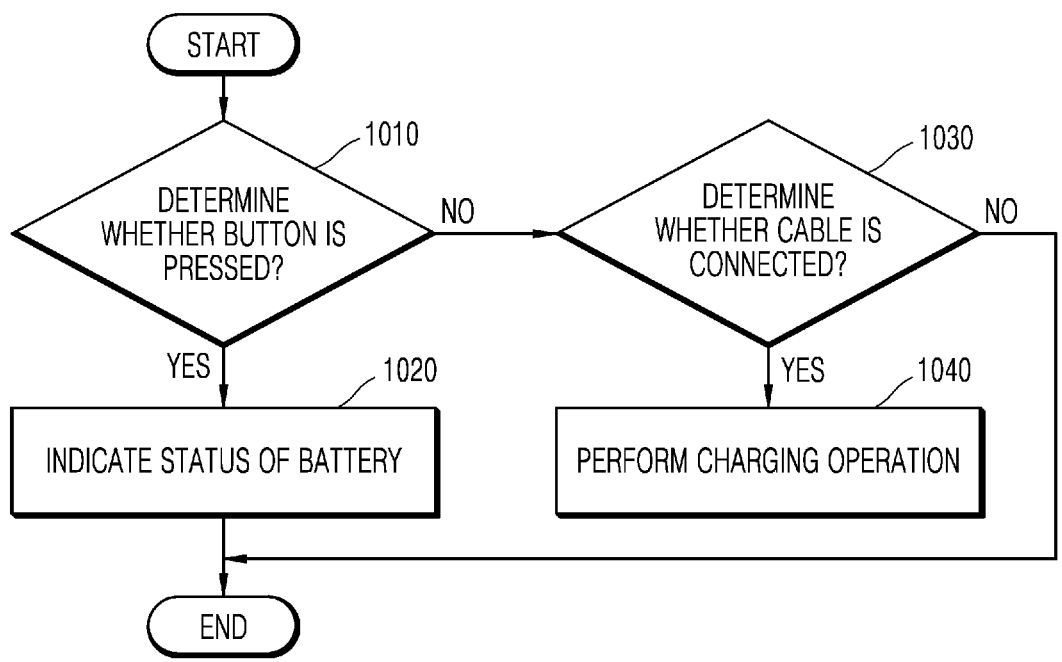
FIG. 18 is a flowchart for describing an example in which a cradle operates.

FIG. 18 is a flowchart for describing an example in which a cradle operates.

The flowchart shown in FIG. 18 includes operations that are performed in a time-series manner by the cradle 2 shown in FIG. 2. Therefore, it will be understood that the descriptions given above with respect to the cradle 2 shown in FIG. 11 also apply to the method of FIG. 18, even when the descriptions are omitted below.

Although not shown in FIG. 18, the operation of the cradle 2 to be described below may be performed regardless of whether the holder 1 is inserted into the cradle 2.

In operation 1010, the control unit 220 of the cradle 2 determines whether the button 240 is pressed. When the button 240 is pressed, the method proceeds to operation 1020. When the button 240 is not pressed, the method proceeds to operation 1030.

In operation 1020, the cradle 2 indicates the status of the battery 210. For example, the control unit 220 may output information regarding the current state of the battery 210 (e.g., remaining power, etc.) on the display 250.

In operation 1030, the control unit 220 of the cradle 2 determines whether a cable is connected to the cradle 2. For example, the control unit 220 determines whether a cable is connected to an interface (e.g., a USB port, etc.) included in the cradle 2. When a cable is connected to the cradle 2, the method proceeds to operation 1040. Otherwise, the method is terminated.

In operation 1040, the cradle 2 performs a charging operation. For example, the cradle 2 charges the battery 210 by using power supplied through a connected cable.

As described above with reference to FIG. 9, a cigarette may be inserted into the holder 1. The cigarette includes an aerosol generating material and aerosol is generated by the heated heater 130.

Hereinafter, an example of a cigarette that may be inserted into the holder 1 will be described with reference to FIGS. 19 to 21f.

Figure 19:
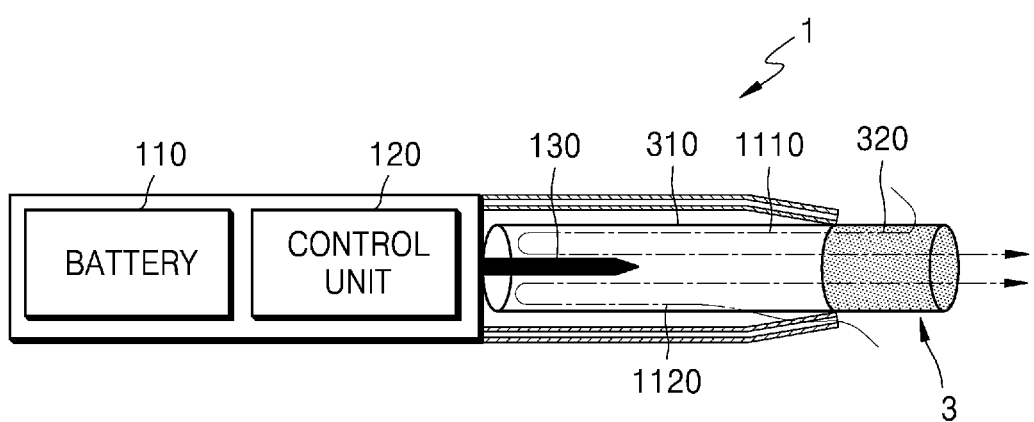
FIG. 19 is a diagram showing an example in which a cigarette is inserted into a holder.

FIG. 19 is a diagram showing an example in which a cigarette is inserted into a holder.

Referring to FIG. 19, the cigarette 3 may be inserted into the holder 1 through the terminal end 141 of the casing 140. When the cigarette 3 is inserted into the holder 1, the heater 130 is located inside the cigarette 3. Therefore, the heated heater 130 heats the aerosol generating material of the cigarette 3, thereby generating aerosol.

The cigarette 3 may be similar to a typical burning cigarette. For example, the cigarette 3 may include a first portion 310 containing an aerosol generating material and a second portion 320 including a filter and the like. Meanwhile, the cigarette 3 according to one embodiment may also include an aerosol generating material in the second portion 320. For example, an aerosol generating material in the form of granules or capsules may be inserted into the second portion 320.

The entire first portion 310 may be inserted into the holder 1 and the second portion 320 may be exposed to the outside. Alternatively, only a portion of the first portion 310 may be inserted into the holder 1 or the entire first portion 310 and a portion the second portion 320 may be inserted into the holder 1.

A user may inhale the aerosol while holding the second portion 320 by his/her lips. At this time, the aerosol is mixed with the outside air and is delivered to a user's mouth. As shown in FIG. 19, the outside air may be introduced (1110) through at least one hole formed in a surface of the cigarette 3, or introduced (1120) through at least one air passage formed in the holder 1. For example, the opening and closing of the air passage formed in the holder 1 may be adjusted by a user.

Figure 20A:
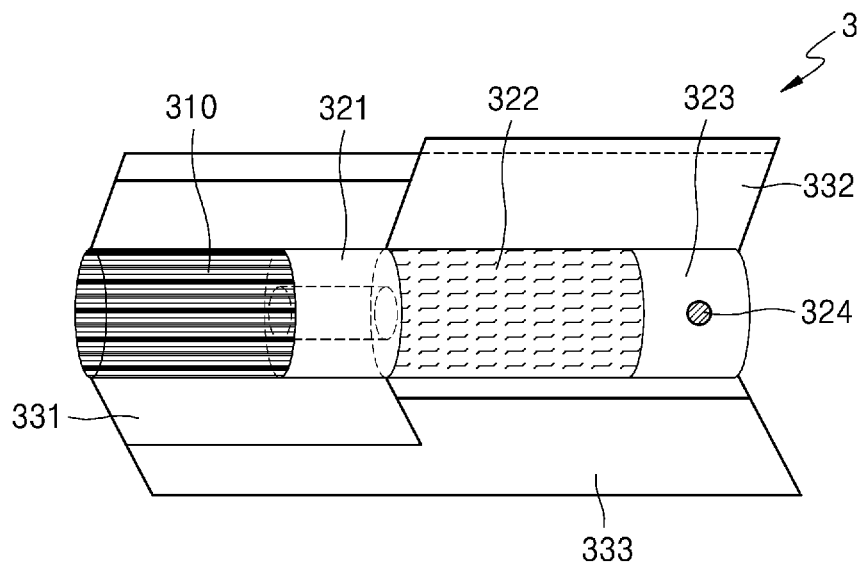
FIGS. 20A and 20B are block diagrams showing examples of a cigarette.
Figure 20B:
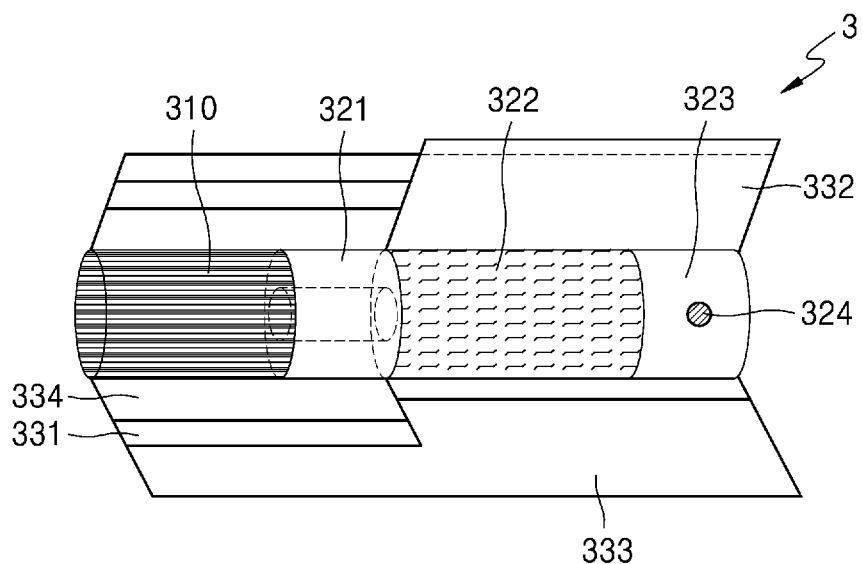

FIGS. 20A and 20B are block diagrams showing examples of a cigarette.

Referring to FIGS. 20A and 20B, the cigarette 3 includes a tobacco rod 310, a first filter segment 321, a cooling structure 322, and a second filter segment 323. The first portion 310 described above with reference to FIG. 19 includes the tobacco rod 310 and the second portion 320 includes the first filter segment 321, the cooling structure 322, and the second filter segment 323.

Meanwhile, referring to FIGS. 20A and 20B, the cigarette 3 shown in FIG. 20B further includes a fourth wrapper 334 compared to the cigarette 3 shown in FIG. 20A.

But, the features of cigarette 3 shown in FIGS. 20a, 20b are examples with some elements omitted. For example, the cigarette 3 may not include one or more of the first filter segment 321, the cooling structure 322, and the second filter segment 323.

The tobacco rod 310 includes an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol. The tobacco rod 310 may have a length ranged between 7 mm to 15 mm, preferably about 12 mm. Also, the tobacco rod 310 may have a diameter ranged between 7 mm to 9 mm, preferably about 7.9 mm. The length and diameter of tobacco rod 310 are not limited to the above range.

Also, the tobacco rod 310 may include other additive materials like a flavoring agent, a wetting agent, and/or acetate compound. For example, the flavoring agent may include licorice, sucrose, fructose syrup, isosweet, cocoa, lavender, cinnamon, cardamom, celery, fenugreek, cascara, sandalwood, bergamot, geranium, honey essence, rose oil, vanilla, lemon oil, orange oil, mint oil, cinnamon, keragene, cognac, jasmine, chamomile, menthol, cinnamon, ylang ylang, salvia, spearmint, ginger, coriander, coffee, etc. In addition, the wetting agent may include glycerin or propylene glycol.

For example, the tobacco rod 310 may be filled with cut tobacco leaves. Here, cut tobacco leaves may be formed by fine-cutting a tobacco sheet.

For a large wide tobacco sheet to be filled within the tobacco rod 310 having a narrow space, a special operation for facilitating folding of the tobacco sheet is further needed. Therefore, it is easier to fill the tobacco rod 310 with cut tobacco leaves compared to filling the tobacco rod 310 with a tobacco sheet, and thus the productivity and the efficiency of the process for producing the tobacco rod 310 may be improved.

In another example, the tobacco rod 310 may be filled with a plurality of cigarette strands formed by fine-cutting a tobacco sheet. For example, the tobacco rod 310 may be formed by combining a plurality of tobacco strands in the same direction (parallel to one another) or randomly. One tobacco strand may be formed into a cuboid shape with 1 mm width, 12 mm depth, and 0.1 mm height, but not limited thereto.

The tobacco rod 310 filled with tobacco strands may generate much more aerosol than tobacco rod 310 filled with tobacco sheet. By filling the tobacco rod with tobacco strands, wider surface area can be secured compared to using tobacco sheet. A wider surface area indicates that an aerosol generating material has a greater chance of contacting the outside air. Therefore, when the tobacco rod 310 is filled with tobacco strands, the tobacco rod can generate much more aerosol compared to when being filled with tobacco sheet.

Also, when the cigarette 3 is being disengaged from the holder 1, the tobacco rod 310 filled with tobacco strands can be easily pulled out compared to when being filled with tobacco sheet. Compared to tobacco sheet, the tobacco strands experience weaker friction when in contact with the heater 130. Therefore, when the tobacco rod 310 is filled with tobacco strands, the tobacco rod can be more easily removed from the holder 1 compared to when being filled with tobacco sheet.

The tobacco sheet can be formed by pulverizing raw tobacco material into a slurry and drying the slurry. For example, the slurry may contain 15% to 30% aerosol generating material. The raw tobacco material may be tobacco leaf fragments, tobacco stems, and/or fine tobacco powders formed during treatment of tobacco. The tobacco sheet may also include other additives like wood cellulose fibers.

The first filter segment 321 may be a cellulose acetate filter. For example, the first filter segment 321 may have a tubular structure including a hollowness therein. The length of the first filter segment 321 may be any suitable length within the range from 7 mm to 15 mm, preferably about 7 mm, but is not limited thereto. The length of the first filter segment 321 may be smaller than about 7 mm, but the first filter segment preferably should have enough length so that function of at least one of components (such as, cooling element, capsule, acetate filter) may not be damaged. The length of the first filter segment 321 is not limited to the above ranges. Meanwhile, the length of the first filter segment 321 may extended so that whole length of the cigarette 3 can be adjusted based on the length of the first filter segment 321.

The second filter segment 323 may also be a cellulose acetate filter. For example, the second filter segment 323 may be fabricated as a recess filter with a hollow cavity, but is not limited thereto. The length of the second filter segment 323 may be within the range from 5 mm to 15 mm, preferably about 12 mm. The length of the second filter segment 323 is not limited to above range.

Also, the second filter segment 323 may include at least one capsule 324. Here, the capsule 324 may have a structure in which a content liquid containing a flavoring material is wrapped with a film. For example, the capsule 324 may have a spherical or cylindrical shape. The capsule 324 may have a diameter equal to or greater than 2 mm, preferably ranged between 2-4 mm.

A material forming a surface of the capsule 324 may be starch and/or gellant. For example, the gallant may include gelatin, or a gum. Also, a gelling agent may be further used as a material for forming the film of the capsule 324. Here, gelling agent may include, for example, a calcium chloride. Furthermore, a plasticizer may be further used as a material for forming the film of the capsule 324. As the plasticizer, glycerin and/or sorbitol may be used. Furthermore, a coloring agent may be further used as a material for forming the film of the capsule 324.

For example, as a flavoring material included in the content liquid of the capsule 324, menthol, plant essential oil, and the like may be used. As a solvent of the flavoring material included in the content liquid, for example, a medium chain fatty acid triglyceride (MCT) may be used. Also, the content liquid may include other additives like a figment, an emulsifying agent, a thickening agent, etc.

The cooling structure 322 cools aerosol generated as the heater 130 heats the tobacco rod 310. Therefore, a user may inhale aerosol cooled to a suitable temperature. The length of the cooling structure 322 may be ranged between about 10 mm to 20 mm, preferably about 14 mm. The length of the cooling structure 322 is not limited to the above range.

For example, the cooling structure 322 may be formed by polylactic acid. The cooling structure 322 may be fabricated into various shapes in order to increase a surface area per unit area, namely, a surface area contacting with aerosol. Hereinafter, Various examples of the cooling structure 322 will be explained referring to FIGS. 21a to 21f.

The tobacco rod 310 and the first filter segment 321 are packed by a first wrapper 331. For example, the first wrapper 331 may be made of an oil-resistant paper sheet.

The cooling structure 322 and the second filter segment 323 are packed by a second wrapper 332. Also, a whole part of cigarette 3 is packaged again by a third wrapper 333. For example, the second wrapper 332 and the third wrapper 333 may be fabricated using a general filter wrapping paper. Alternatively, the second wrapper 332 may be a hard wrapping paper or PLA scented paper. Also, the second wrapper 332 may package a part of the second filter segment 323, and additionally package other part of the second filter segment 323 and the cooling structure 322.

Referring to FIG. 20B, the cigarette 3 may include a fourth wrapper 334. At least one of the cigarette rod 310, the first filter segment 321 may be packaged by the fourth wrapper 334. In other words, only the cigarette rod 310 may be packaged by the fourth wrapper 334, or the cigarette rod 310 and the first filter segment 321 are packaged together by the fourth wrapper 334. For example, the fourth wrapper 334 may be made of wrapping paper.

The fourth wrapper 334 may be formed by depositing or coating a predetermined material on one surface or both surfaces of wrapping paper. Here, an example of the predetermined material may be, but is not limited to, silicon. Silicon exhibits characteristics like heat resistance with little change due to the temperature, oxidation resistance, resistances to various chemicals, water repellency, electrical insulation, etc. However, any material other than silicon may be applied to (or coated on) the fourth wrapper 334.

Meanwhile, although FIG. 20B shows that the cigarette 3 includes both the first wrapper 331 and the fourth wrapper 334, but the embodiment is not limited thereto. In other words, the cigarette 3 may include only one of the first wrapper 331 and the fourth wrapper 334.

The fourth wrapper 334 may prevent the cigarette 3 from being burned. For example, when the tobacco rod 310 is heated by the heater 130, there is a possibility that the cigarette 3 is burned. In detail, when the temperature is raised to a temperature above the ignition point of any one of materials included in the tobacco rod 310, the cigarette 3 may be burned. Even in this case, since the fourth wrapper 334 includes a non-combustible material, the burning of the cigarette 3 may be prevented.

Furthermore, the fourth wrapper 334 may prevent the holder 1 from being contaminated by substances formed by the cigarette 3. Through puffs of a user, liquid substances may be formed in the cigarette 3. For example, as the aerosol formed by the cigarette 3 is cooled by the outside air, liquid materials (e.g., moisture, etc.) may be formed. As the fourth wrapper 334 wraps the tobacco rod 310 and/or the first filter segment 321, the liquid materials formed in the cigarette 3 may be prevented from being leaked out of the cigarette 3. Accordingly, the casing 140 of the holder 1 and the like may be prevented from being contaminated by the liquid materials formed by the cigarette 3.

FIGS. 21A through 21F are views illustrating cooling structures of a cigarette.

For example, the cooling structure of any of FIGS. 21A through 21F may be manufactured by using fibers made of pure polylactic acid (PLA).

For example, when the cooling structure is manufactured by charging a film (sheet), the film (sheet) may be crushed by an external impact. In this case, an aerosol cooling effect of the cooling structure is reduced.

Alternatively, when the cooling structure is manufactured by using extrusion molding or the like, process efficiency is reduced due to the addition of processes such as cutting of a structure. Also, there are limitations in manufacturing the cooling structure in various shapes.

As the cooling structure according to an embodiment is manufactured by using polylactic acid fibers (e.g., weaving), the risk that the cooling structure is deformed or loses its function by an external impact may be reduced. Also, the cooling structure having various shapes may be manufactured by changing a method of combining fibers.

Also, when the cooling structure is manufactured by using fibers, a surface area contacting aerosol is increased. Accordingly, an aerosol cooling effect of the cooling structure may be further improved.

Figure 21A:
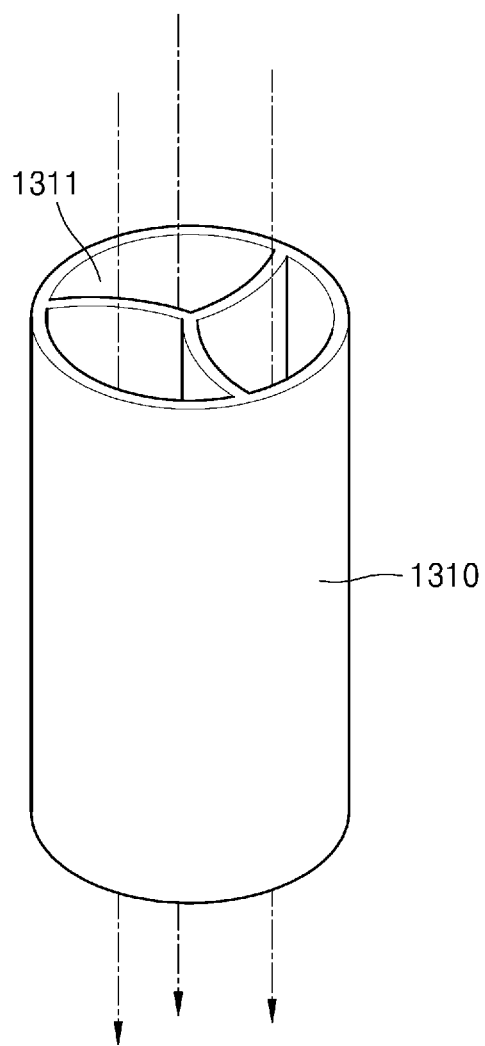
FIGS. 21A through 21F are views illustrating examples of a cooling structure of a cigarette.

Referring to FIG. 21A, a cooling structure 1310 may have a cylindrical shape, and may be formed so that at least one air passage 1311 is formed in a cross-section of the cooling structure 1310.

Figure 21B:
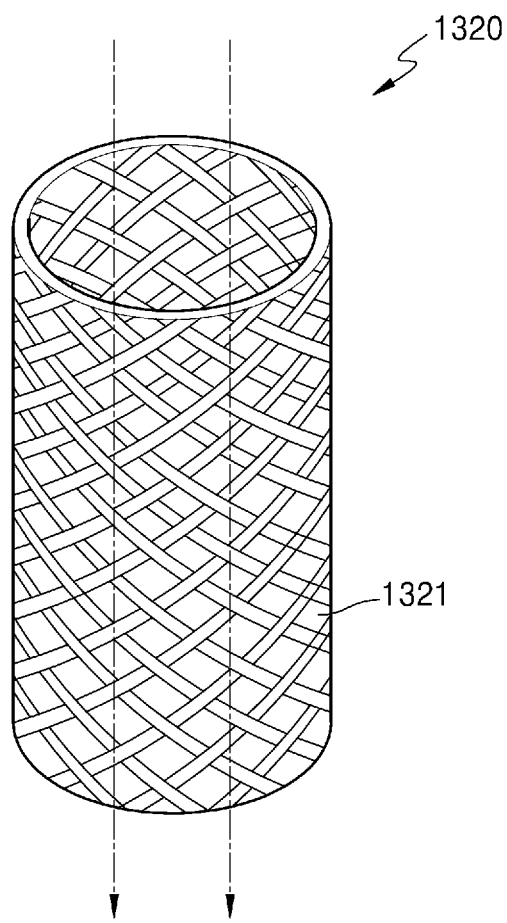

Referring to FIG. 21B, a cooling structure 1320 may be manufactured so that a plurality of fibers are tangled with one another. In this case, aerosol may flow between the fibers, and a vortex may be formed according to a type of the cooling structure 1320. The vortex increases a contact area of the aerosol in the cooling structure 1320 and increases a time during which the aerosol stays in the cooling structure 1320. Accordingly, heated aerosol may be effectively cooled.

Figure 21C:
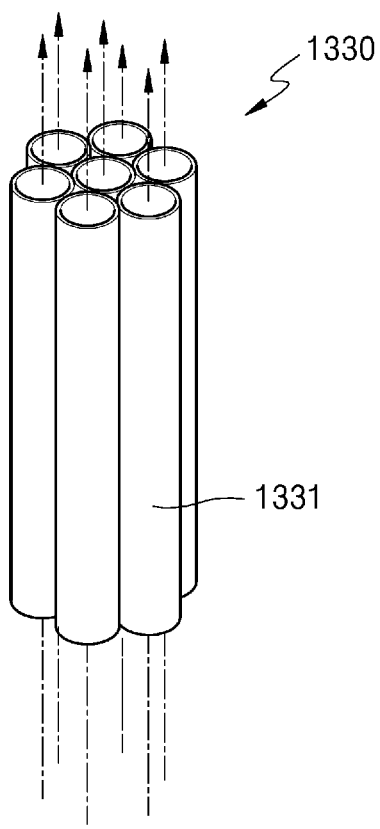

Referring to FIG. 21C, a cooling structure 1330 may be manufactured in a shape in which a plurality of bundles 1331 are gathered.

Figure 21D:
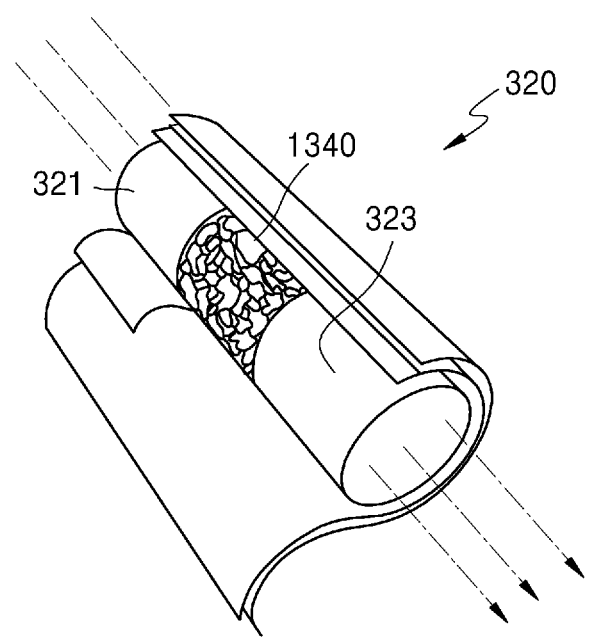

Referring to FIG. 21D, a cooling structure 1340 may be filled with granules formed of PLA, cut leaves, or charcoal. Also, the granules may be fabricated by using a mixture of PLA, cut leaves, and charcoal. On the other hand, the granules may further include an element capable of increasing an aerosol cooling effect in addition to the PLA, the cut leaves, and/or the charcoal.

Figure 21E:
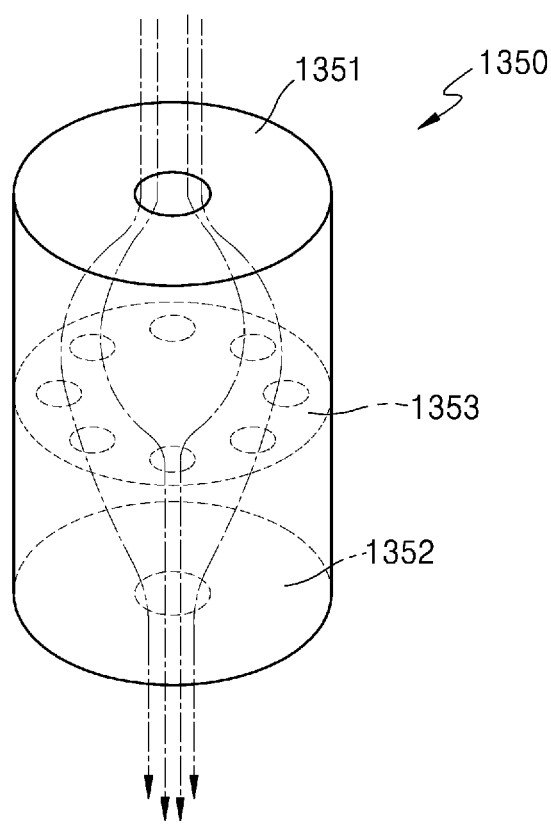

Referring to FIG. 21E, a cooling structure 1350 may include a first cross-section 1351 and a second cross-section 1352.

The first cross-section 1351 may border on the first filter segment 321, and may include a gap through which aerosol is introduced. The second cross-section 1352 may border on the second filter segment 323, and may include a gap through which the aerosol may be discharged. For example, although each of the first cross-section 1351 and the second cross-section 1352 may include a single gap having the same diameter, diameters and numbers of gaps included in the first cross-section 1351 and the second cross-section 1352 are not limited thereto.

In addition, the cooling structure 1350 may include a third cross-section 1353 including a plurality of gaps between the first cross-section 1351 and the second cross-section 1352. For example, diameters of the plurality of gaps included in the third cross-section 1353 may be less than diameters of the gaps included in the first cross-section 1351 and the second cross-section 1352. Also, the number of the gaps included in the third cross-section 1353 may be greater than the number of the gaps included in the first cross-section 1351 and the second cross-section 1352.

Figure 21F:
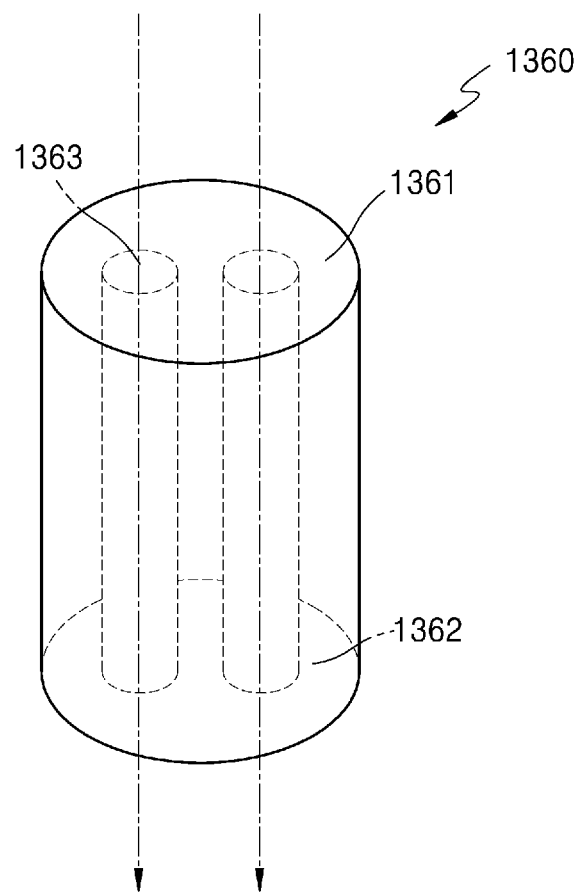

Referring to FIG. 21F, a cooling structure 1360 may include a first cross-section 1361 that borders on the first filter segment 321 and a second cross-section 1362 that borders on the second filter segment 323. Also, the cooling structure 1360 may include one or more tubular elements 1363. For example, each of the tubular elements 1363 may pass through the first cross-section 1361 and the second cross-section 1362. Also, the tubular element 1363 may be packaged with a microporous packaging material, and may be filled with a filling material (e.g., the granules of FIG. 21D) that may increase an aerosol cooling effect.

As described above, a holder may generate aerosol may heating a cigarette. Also, aerosol may be generated independently by the holder or even when the holder is inserted into a cradle and is tilted. In particular, when the holder is tilted, a heater may be heated by power of a battery of the cradle.

The embodiments of the present disclosure may be written as computer programs and may be implemented in general-use digital computers that execute the programs using a computer-readable recording medium. In addition, a structure of data used in the method may be recorded on a computer-readable recording medium through various means. Examples of the computer-readable recording medium include magnetic storage media (e.g., read-only memory (ROM), random-access memory (RAM), universal serial bus (USB) drives, floppy disks, hard disks, etc.), optical recording media (e.g., compact disc (CD)-ROMs, or digital versatile disks (DVDs)), etc.

It will be understood by one of ordinary skill in the art that various changes in form and details may be made therein without departing from the spirit and scope of the present disclosure as defined by the appended claims. Therefore, the disclosed methods should be considered from an illustrative point of view, not from a restrictive point of view. The scope of the present disclosure is defined by the appended claims rather than by the foregoing description, and all differences within the scope of equivalents thereof should be construed as being included in the present disclosure.

INDUSTRIAL APPLICABILITY

Embodiments may be applied to a heated cigarette or a heated aerosol generating device that generates aerosol by heating an aerosol generating material in a cigarette.

What is claimed is:
1. An aerosol generating device comprising:
   a casing having an inner space that provides a path for accommodating a cigarette;
   a rotating member rotatably coupled to the casing, and exposed to an outside of the casing such that the rotating member is rotatable by a user; and
   a heater having an end portion located inside the path such that the end portion is inserted into and heats the cigarette accommodated in the path, and connected to the rotating member such that the heater rotates along with the rotating member.
2. The aerosol generating device of claim 1, wherein
   the rotating member rotates about a central axis in a longitudinal direction of the path.

3. The aerosol generating device of claim 2, wherein the heater rotates about the central axis in the longitudinal direction of the path.

4. The aerosol generating device of claim 1, further comprising
a connector connecting the rotating member to the heater and rotating along with the rotating member and the heater.

5. The aerosol generating device of claim 4, wherein
a protruding portion is provided on one of the connector and the rotating member,
a groove portion is provided on the other of the connector and the rotating member so that the protruding portion is inserted into the groove portion, and
the casing further comprises an intermediate container having a guide hole which allows the protruding portion to pass therethrough and extends in a circumferential direction of the rotating member to provide a movement path for the protruding portion while the rotating member rotates.

6. The aerosol generating device of claim 5, wherein
the intermediate container further comprises a rotation limiter configured to limit movement of the protruding portion.

7. The aerosol generating device of claim 4, wherein
the connector has a through-hole through which the end portion of the heater passes,
a coupling protrusion is provided on one of the heater and an inner surface of the connector,
a coupling groove is provided on the other of the heater and the through-hole so that the coupling protrusion is inserted into the coupling groove.

8. The aerosol generating device of claim 5, further comprising
a pressing member provided in a path in which the protruding portion moves and configured to apply an elastic force with respect to movement of the protruding portion.

9. The aerosol generating device of claim 5, wherein the casing further comprises:
an inner container having an inner space that provides the path in which the cigarette is accommodated, and located inside the intermediate container; and
an outer container for accommodating the intermediate container.

10. The aerosol generating device of claim 9, further comprising
a cap coupled to an end portion of the inner container and having a hole through which the end portion of the heater passes.

11. The aerosol generating device of claim 5, wherein
a movement protrusion is provided on one of the rotating member and the casing, and
a guide groove portion extending in the circumferential direction of the rotating member is provided on the other of the rotating member and the casing so that the movement protrusion is inserted into the guide groove portion and movement of the protruding portion is guided by the guide groove portion.

* * * * *